United States Patent
Laukkanen et al.

(10) Patent No.: US 9,593,304 B2
(45) Date of Patent: Mar. 14, 2017

(54) THREE-DIMENSIONAL DISCONTINUOUS ENTITY FOR CELL CULTURING

(71) Applicant: UPM-Kymmene Corporation, Helsinki (FI)

(72) Inventors: Antti Laukkanen, Helsinki (FI); Yan-Ru Lou, Helsinki (FI); Marjo Yliperttula, Espoo (FI); Tytti Kuisma, Helsinki (FI); Johanna Nikander, Helsinki (FI); Jaakko Pere, Vantaa (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 0 days.

(21) Appl. No.: 14/430,833

(22) PCT Filed: Sep. 24, 2013

(86) PCT No.: PCT/FI2013/050928
§ 371 (c)(1),
(2) Date: Mar. 24, 2015

(87) PCT Pub. No.: WO2014/049204
PCT Pub. Date: Apr. 3, 2014

(65) Prior Publication Data
US 2015/0267164 A1 Sep. 24, 2015

(30) Foreign Application Priority Data

Sep. 25, 2012 (FI) ...................................... 20125997

(51) Int. Cl.
| | | |
|---|---|---|
| C12N 5/02 | (2006.01) | |
| C12N 5/071 | (2010.01) | |
| C12N 5/00 | (2006.01) | |
| C12N 5/0735 | (2010.01) | |
| C12N 5/074 | (2010.01) | |

(52) U.S. Cl.
CPC ......... *C12N 5/0602* (2013.01); *C12N 5/0062* (2013.01); *C12N 5/0606* (2013.01); *C12N 5/0696* (2013.01); *C12N 2500/92* (2013.01); *C12N 2533/78* (2013.01)

(58) Field of Classification Search
None
See application file for complete search history.

(56) References Cited

U.S. PATENT DOCUMENTS

| | | |
|---|---|---|
| 3,775,252 A | 11/1973 | Kinsel et al. |
| 5,254,471 A | 10/1993 | Mori et al. |
| 5,558,861 A | 9/1996 | Yamanaka et al. |
| 5,963,419 A | 10/1999 | Tanaka et al. |
| 6,602,994 B1 | 8/2003 | Cash et al. |
| 8,691,974 B2 * | 4/2014 | Gatenholm ............. A61L 27/20 435/170 |
| 2007/0053960 A1 | 3/2007 | Brown |
| 2007/0172938 A1 | 7/2007 | Deguchi et al. |
| 2007/0275458 A1 | 11/2007 | Gouma |
| 2008/0146701 A1 | 6/2008 | Sain et al. |
| 2009/0028927 A1 | 1/2009 | Wan et al. |
| 2009/0053276 A1 | 2/2009 | Richard |
| 2009/0123990 A1 | 5/2009 | Bergmaier |
| 2009/0305412 A1 | 12/2009 | Ying |
| 2010/0065236 A1 | 3/2010 | Henriksson et al. |
| 2010/0124783 A1 | 5/2010 | Chen et al. |
| 2010/0172889 A1 | 7/2010 | Catchmark |
| 2010/0172952 A1 * | 7/2010 | Srouji ..................... A61L 27/46 424/423 |
| 2010/0233234 A1 | 9/2010 | Arinzeh et al. |
| 2010/0233245 A1 | 9/2010 | Narayana |
| 2011/0015387 A1 | 1/2011 | Schuth et al. |
| 2011/0117319 A1 | 5/2011 | Yano et al. |
| 2011/0198282 A1 | 8/2011 | Chu et al. |
| 2012/0040461 A1 * | 2/2012 | Beachley ................ A61L 27/48 435/396 |
| 2013/0011385 A1 | 1/2013 | Li et al. |
| 2013/0344036 A1 * | 12/2013 | Yliperttula ............... A61K 9/06 424/93.7 |
| 2014/0010790 A1 * | 1/2014 | Yliperttula ............... A61K 9/06 424/93.7 |
| 2014/0349377 A1 | 11/2014 | Lauraeus et al. |
| 2015/0010980 A1 | 1/2015 | Lauraeus et al. |
| 2015/0064142 A1 * | 3/2015 | Green ..................... A61L 27/18 424/93.7 |
| 2015/0100121 A1 * | 4/2015 | Lu ........................... A61K 38/18 623/13.12 |

FOREIGN PATENT DOCUMENTS

| | | |
|---|---|---|
| CN | 1718172 | 1/2006 |
| CN | 1730734 | 2/2006 |
| CN | 101288778 A | 10/2008 |
| CN | 101392246 A | 3/2009 |
| EP | 0243151 A2 | 10/1987 |

(Continued)

OTHER PUBLICATIONS

Xing, Qi. Micro, Nano Integrated Composites Based on Cellulose Microfibers. Dissertation Abstracts 71(3 Supp B) Nov. 2009.*
Bhattacharya et al., "Nanofibrillar cellulose hydrogel promotes three-dimensional liver cell culture"; J. Controlled Release, 2012, vol. 164, pp. 291-298.
Deguchi et al., "Preparation and characterisation of nanofibrous cellulose plate as a new solid support for microbial culture"; Soft Matter, 2007, vol. 3, pp. 1170-1175.
Tsudome et al., "Versatile Solidified Nanofibrous Cellulose-Containing Media for Growth of Extremophiles"; Applied and Environmental Microbiology, 2009, pp. 4616-4619.

(Continued)

*Primary Examiner* — Ralph Gitomer
(74) *Attorney, Agent, or Firm* — Nixon Peabody LLP

(57) ABSTRACT

The present invention is related to methods and materials for culturing and transporting stem cells in a three-dimensional culture. The materials comprise cellulose nanofibrils in a form of three-dimensional discontinuous entities in a biocompatible hydrogel.

23 Claims, 16 Drawing Sheets

(56) References Cited

FOREIGN PATENT DOCUMENTS

| | | |
|---|---|---|
| JP | 02-081738 | 3/1990 |
| JP | 2004-090791 | 3/2004 |
| JP | 2004-249928 | 9/2004 |
| JP | 2006-008028 | 1/2006 |
| JP | 2008308802 A | 12/2008 |
| WO | 9831785 A1 | 7/1998 |
| WO | 2007012050 A2 | 1/2007 |
| WO | 2009126980 A1 | 10/2009 |
| WO | 2010135234 A2 | 11/2010 |
| WO | 2012056109 A2 | 5/2012 |
| WO | 2012056110 A2 | 5/2012 |

OTHER PUBLICATIONS

Finnish Search Report, dated Sep. 5, 2012, from Application No. FI 20116316.
International Search Report, dated Apr. 2, 2013, from PCT Application No. PCT/FI2012/051264.
Ramirez-Arcos, S. et al.; "A thermophilic nitrate reductase is responsible for the strain specific anaerobic growth of Thermus thermophilus HB8." Biochimica et Biophysica Acta. 1998, 1936:215-227.
Czaja et al.; "The Future Prospects of Microbial Cellulose in Biomedical Applications"; Biomacromolecules, 2007, vol. 3, No. 1, pp. 1-12.
Czaja W. et al.: "Microbial cellulose—the natural power to heal wounds", Biomaterials, vol. 27, No. 2. Jan. 2006 (Jan. 2006), pp. 145-151, XP025096958, ISSN: 0142-9612.001:10.1 016/J.BIOMATERIAIS.2005.07.035 [retrieved on Jan. 1, 2006].
Muller A. et al.: "Bacterial nanocellulose wound dressing as drug delivery system", American Chemical Society. Abstracts of Paper; 239th National Meeting of the American Chemical Society, US; San Francisco. CA. US, vol. 239, Cell-22, Mar. 21, 2010 (Mar. 21, 2010), XP008151040, ISSN: 0065-7727.
Elzinga G. et al.: "Clinical evaluation of a PHMB-impregnated biocellulose dressing on paediatric lacerations", J. Wound Care, vol. 20, No. 6; Jun. 2011 (Jun. 2011); pp. 280-284. XP55025495, ISSN: 0969-0700.
Valo H. et al.:" Immobilization of protein-coated drug nanoparticles in nanofibrillar cellulose matrices-Enhanced stability and release", Journal of Controlled Release, vol. 156, No. 3, Dec. 2011 (Dec. 2011), pp. 390-397. XP55025318, ISSN: 0168-3659. DOI: 10.1 016/j.jcomel.2011.07.016 [retrieved on Jul. 23, 2011] online publication Jul. 23, 2011.
Trovatti E. et al.: "Biocellulose Membranes as Supports for Dermal Release of Lidocaine", Biomacromolecules, vol. 12, No. 11, Nov. 14, 2011 (Nov. 14, 2011), pp. 4162-4168. XP55025497, ISSN: 1525-7797. DOI: 10.1021/bm201303r [retrieved on Oct. 16, 2011] online publication Oct. 16, 2011.
Svensson A et al: "Bacterial cellulose as a potential scaffold for tissue engineering of cartilage", Biomaterials, vol. 26. No. 4. Feb. 2005 (Feb. 2005), pp. 419-431, XP025280897, ISSN: 0142-9612, DOI: 10.1 016/J. Biomaterials, 2004.02.049 D [retrieved on Feb. 1, 2005].
Backdahl H. et al: "Mechanical properties of bacterial cellulose and interactions with smooth muscle cells", Biomaterials, vol. 27. No. 9. Mar. 2006 (Mar. 2006), pp. 2141-2149. XP025097665, ISSN: 0142-9612, DOI: 10 .1016/J.BIOMATERIALS.2005.1 0.026 D [retrieved on Mar. 1, 2006].
Bodin A. et al.: "Modification of Nanocellulose with a Xyloglucan-RGD Conjugate Enhances Adhesion and Proliferation of Endothelial Cells: Implications for Tissue Engineering", Biomacromolecules, vol. 8, No. 12, pp. D 3697-3704. XP55025397, ISSN: 1525-7797, DOI: 10.1021/bm070343q.
Sanchavanakit N. et al.: "Growth of Human Keratinocytes and Fibroblasts on Bacterial Cellulose Film", Biotechnology Progress, vol. 22. No. 4, Aug. 4, 2006 (Aug. 4, 2006), pp. 1194-1199. XP55025385, D ISSN: 8756-7938, DOI: 10.1021/bp0600350.
Wiegand C. et al.: "HaCaT keratinocytes in co-culture with *Staphylococcus aureus* can be protected from bacterial damage by polihexanide", Wound Repair & Regeneration, vol. 17. No. 5. Sep. 2009 (Sep. 2009), pp. D 130-738. XP55016133, ISSN: 1067-1927. DOI: 10.1111/j.1524-475X.2009.00536.x.
Grande C J. et al.: "Nanocomposites of bacterial cellulose/hydroxyapatite for biomedical applications", Acta Biomaterialia, vol. 5. No. 5. Jun. 2009 (Jun. 2009). pp. 1605-1615. XP026090223, ISSN: 1742-7061. DOI: 10.1016/ J.ACTBI0.2009.01.022 D [retrieved on Jan. 31, 2009].
Database WPI, Week 200930, Thomson Scientific. London. GB; AN 2009-H01547; XP002674558;—& CN 101 392 246 A (UN IV Northeast Electric Power) Mar. 25, 2009 (Mar. 25, 2009) abstract.
International Search Report of PCT/FI2011/050940 mailed Jul. 5, 2012.
International Preliminary Report on Patentability of PCT/FI2011/050940 mailed Mar. 7, 2013.
Ping, W. et al. 'Study on the feasibility of bacterial cellulose as tissue engineering scaffold', Multi-Functional Materials and Structures II, 2nd International Conference on Multi-Functional Materials and Structures, Advanced Materials D Research, 2009, vols. 79-82, p. 147-150.
Evenou F. et al.: "Microfibrillated cellulose sheets coating oxygen-permeable PDMS membranes induce rat hepatocytes 3D aggregation into stably-attached 3D hemispheroids."; J. Biomater. Sci. Polym. Ed. 2011 , vol. 22, No. 11, p. 1509-1522. XP002674465; and Database Medline [Online]; US National Library of Medicine D (NLM); Bethesda. MD, US; Jul. 12, 2010 (Jul. 12, 2010); Database accession No. NLM20626957 abstract.
Recouvreux, D.O.S. et al. Novel three-dimensional cocoon-like hydrogels for soft tissue regeneration. Mater. Sci. Eng. C Mar. 2011, vol. 31, No. 2, p. 151-157. Available online (Epub) Aug. 13, 2010.
Office Action with Search Report dated Jun. 9, 2011 of FI 20106121.
Cai, Z. et al.; "Preparation and characterization of novel bacterial cellulose/gelatin scaffold for tissue regeneration using bacterial cellulose hydrogel"; J. Nanotech. in Engineering and Medicine—Transactions of the ASME; vol. 1 (2010).
Degushi et al.; "Nanofibrous cellulose as novel solid support for microbial culture"; Polymer Preprints, Japan, 57 (1):1811 (2008).
Mugishima et al.; "Cultivation of Tissue Cells Using Cellulose Fibrils and Functional Analysis Thereof"; Fiber Preprints 65(1) Annual Meeting (2010).
Teramoto et al.; "Cell Culturing of Osteoblasts Using Cellulose Nanofibers"; 288 Regenerative Medicine, vol. 6 Suppl. (2007).
Celish, Tiara; Website of Daicel FineChem Ltd., www.daicelfinechem.jp/business/wspdiv/celish.html, retrieved Mar. 25, 2016.
Klemm et al.; "Nanocellulose as innovative polymers in research and application"; Advances in Polymer Science 205: 49-96 (2006).
Henriksson et al.; "An environmentally friendly method for enzyme-assisted preparation of microfibrillated cellulose (MFC) nanofibers"; European Polymer Journal 43:3434-3441 (2007).
Sigma "Sigmacell Cellulose type 101 Product sheet"; available from company's website, copyright 2015.
Acumedia "LB Broth, Lennox (7290)"; available from company's website, Re. 04, Nov. 2010.
Cherian B. M. et al.: "Isolation of nanocellulose from pineapple leaf fibres by steam explosion"; Carbohydrate Polymer, vol. 81. No. 3. Jul. 7, 2010 (Jul. 7, 2010), pp. 720-725. XP027051121, ISSN: 0144-8617 D [retrieved on May 14, 2010].
Borges Acetal: "Nanofibrillated cellulose composite hydrogel for the replacement of the nucleus pulposus", Acta Biomaterialia, vol. 7. No. 9, Sep. 1, 2011 (Sep. 1, 2011), pp. 3412-3421. XP55025311, ISSN: D 1742-7061. DOI: 1 0.1016/j.actbio.2011.05.029.
Paako M. et al.: "Enzymatic Hydrolysis Combined with Mechanical Shearing and High-Pressure Homogenization for Nanoscale Cellulose Fibrils and Strong Gels", Biomacromolecules, vol. 8. No. 6. Jun. 2007 (Jun. 2007). pp. 1934-1941. XP003026928, ISSN: 1525-7797.001: 10.1021/BM061215P D [retrieved on May 3, 2007].
International Search Report for PCT/F12011/050939.
International Preliminary Report on Patentability for PCT/FI2011/050939.

(56) References Cited

OTHER PUBLICATIONS

The State Intellectual Property Office of the People's Republic of China Notice on the First Office Action for Application No. 201180062719.2 mailed Apr. 11, 2014.
Randle, W. et al.; "Integrated 3-Dimensional Expansion and Osteogenic Differentiation of Murine Embryonic Stem Cells"; Tissue Enginerring, vol. 13, No. 12, pp. 2957-2970; 2007; DOI: 10.1089/ten.2007.0072.
Yue, Z. et al.; "Preparation of three-dimensional interconnected macroporous cellulosic hydrogels for soft tissue engineering"; Biomaterials 31 (2010); pp. 8141-8152.
Hwang, Y-S., et al.; "The use of murine embryonic stem cells, alginate encapsulation, and rotary microgravity bioreactor in bone tissue engineering"; Biomaterials 30 (2009) pp. 499-507.
InvitroCue Pte Ltd.; "3D CelluSPonge" web page; from company's website, National University of Singapore; publication date unknown (2 pages).
Popa, E. et al.; "Cell Delivery Systems Using Alginate-Carrageen Hydrogel Beads and Fibers for Regenerative Medicine Applications"; Biomacromolecules; pp. 3952-3961; Oct. 4, 2011 dx.doi.org/10.1021/bm200965x/Biomacromolecules 2011, 12 (10 pages).
Intellectual Property Office of Singapore, Written Opinion for Application No. 11201501729T, mailed May 24, 2016 (7 pages).
International Preliminary Report on Patentability for PCT/JP2013/052770, mailed Aug. 19, 2014.
International Search Report for PCT/JP2013/052770, mailed Mar. 5, 2013.
Yamaguchi, T. et al.; "Examination of the Organization of Cells Using Nanofibers"; Fukuoda Industrial Technology Cancer Research Reports, (2008), in Japanese with English translation.
International Search Report for PCT/FI2012/051266, mailed Apr. 22, 2013.

* cited by examiner

THREE-DIMENSIONAL DISCONTINUOUS ENTITY FOR CELL CULTURING

CROSS-REFERENCE TO RELATED APPLICATIONS

This application is a 35 U.S.C. §371 National Phase Entry Application of International Application No. PCT/FI2013/050928 filed Sep. 24, 2013, and which claims benefit of Finnish Application No.: 20125997 filed Sep. 25, 2012.

SEQUENCE LISTING

The instant application contains a Sequence Listing which has been submitted in ASCII format via EFS-Web and is hereby incorporated by reference in its entirety. Said ASCII copy, created on Sep. 24, 2013, is named 041978-084510_SL.txt and is 1,252 bytes in size.

FIELD OF THE INVENTION

The present invention relates to the field of cell culture systems and cell technology.

BACKGROUND

Human embryonic stem cells (hESCs)[1] and human induced pluripotent stem cells (hiPSCs)[2,3] are self-renewing pluripotent cells that are able to differentiate into many cell types in the body. They hold great promises e.g. for cell therapy, drug research and tissue engineering. Further, it is envisioned in the future human induced pluripotent stem cells, multipotent cells and other undifferentiated cells will be proliferated and directed to differentiate into specific lineages so as to develop differentiated cells or tissues which can be transplanted into human bodies for therapeutic purposes. Human pluripotent stem cells and the differentiated cells that may be derived from them are also powerful scientific tools for studying human cellular and developmental systems.

In order to expand hESCs and hiPSCs and prevent their spontaneous differentiation, some in vitro culture systems have been developed. Conventionally the cells were cultured in these systems on feeder cells[1] and later Matrigel coating[4] was introduced to replace feeder cells in combination with the use of conditioned medium or chemically defined medium, for example, mTeSR1 medium[5]. Matrigel, however, includes poorly defined matrix components and reproduction of optimised cell cultures is difficult because of batch-to-batch variation of the material. More recently, several studies using vitronectin (VN)[6], laminin-511 (LM-511)[7], LM-521, synthetic peptide-acrylate surface[8] or synthetic polymer coating[9] have made progress in developing chemically defined in vitro culture systems for propagation of hESCs and hiPSCs at undifferentiated state. However, all these culture systems are using two-dimensional (2D) surfaces, which do not mimic the in vivo environment of stem cells, called stem cell niche. In addition, cells cultured on 2D surfaces are not easily scalable to larger quantities required for e.g. therapy and research.

Adult stem cells, or somatic stem cells, are undifferentiated cells found throughout the body after differentiation. They are responsible for e.g. organ regeneration and capable of dividing in pluripotent or multipotent state and differentiating into differentiated cell lineages.

Human mesenchymal stem cells (hMSC) display a very high degree of plasticity and are found in virtually all organs with the highest density in bone marrow. HMSCs serve as renewable source for mesenchymal cells and have pluripotent ability of differentiating into several cell lineages, including osteoblasts, chondrocytes, adipocytes, skeletal and cardiac myocytes, endothelial cells, and neurons in vitro upon appropriate stimulation, and in vivo after transplantation.

The stem cell niche is a well-defined complex 3D microenvironment and it regulates stem cell fate by spatially presenting biochemical and physical signals. The cells under physiological conditions not only "cross-talk" between each other but also interact with their cellular microenvironment and the extra-cellular matrix (ECM). The ECM provides structural support to the cells and also contributes to signalling and directing cell fate. Mostly, the ECM is composed of glycosaminoglycans and fibrous proteins such as collagen, elastin, laminin and fibronectin self-assembled into nanofibrillar network.

In 3D cell culturing, a suitable culturing matrix should be able to mimic components of native ECM to provide a scaffold having similar properties with the native ECM, such as structural support for cells and a network of interconnected pores for efficient cell migration and transfer of nutrients to the cells.

Hydrogels, both of synthetic and natural origin, have recently emerged as suitable scaffolds for 3D cell culture. The network of interconnected pores in hydrogels allows retention of a large amount of biological fluid facilitating transport of oxygen, nutrients and waste. Furthermore, most hydrogels can be formed under mild cytocompatible conditions and their biological properties can be modulated by surface chemistry.

Engineered hydrogels with modified mechanical, chemical and biological properties have the potential to mimic the ECM and thus establish their utility in 3D cell culture. Commercial products for 3D cell culturing are for example cell culture matrices PuraMatrix™ (3DM Inc.) and Matrigel (BD Biosciences). PuraMatrix™ is a hydrogel of self-assembled peptide nanofibers which resembles the structure of natural fibrillar collagen in ECM with fiber diameter 5-10 nm. It has also high water content, typically 99.5%. U.S. Pat. No. 7,449,180 and WO 2004/007683 disclose peptide hydrogels. Matrigel is gelatinous protein mixture secreted by mouse tumor cells. The mixture resembles the complex extracellular environment found in many tissues and is used by cell biologists as a substrate for cell culture. MaxGel® ECM Matrix (Sigma-Aldrich), which includes a mixture of human ECM components, forms a gel in ambient temperature. Typically, in these systems the pluripotent cells are separated from the cell culture matrix by protease treatment which breaks extracellular protein network used by the cells to attach themselves to the cell culture matrix and to neighbouring cells.

Bacterial cellulose (BC) has been used in wound healing membranes and as a scaffold in cell culture. The limitation in the use of bacterial cellulose in stem cell culture is the inherent structure of the fermented material: Upon cultivation, BC is formed as very tight membranes in air-water interphase in the fermenter. The formed membranes are too tight for 3D cell culturing and various modifications. If used as cell culture matrix, the porosity of the BC matrix has to be increased for adequate cell penetration and formation of cell clusters.

U.S. Pat. No. 5,254,471 discloses a carrier for cell culture comprising ultra fine fibers. WO 2009/126980 discloses cellulose-based hydrogels whose framework substance consists essentially of or entirely of cellulose and are formed by regeneration from organic solvents. EP1970436B1 discloses carrier material for undifferentiated cell cultures. Present 2D and 3D cell culture systems for pluripotent cell cultures, such as stem cells, rely on animal based matrices. Animal based compounds in cell culture environment generate a risk of immunoreactions and different types of toxicity issues in cell culture and downstream applications. Further, harvesting cells from cell culture matrices composed of proteinaceous material requires treating the cell culture with protein degrading enzyme such as protease, which is also hydrolyses extracellular structures of the cultured cells.

BRIEF DESCRIPTION OF THE INVENTION

Even though many advances have been made in cell culture systems for undifferentiated cells, the prior solutions have not been able to provide a cell culture system which enables scalable 3D culturing and harvesting of undifferentiated cells and spheroids. Further, previous solutions require using animal based chemicals or compounds on the biomaterial media to maintain cell growth and propagation. Maintenance of stem cells in pluripotent state is demanding and requires careful control of culturing conditions, materials and handling of the cells. Further, transporting pluripotent cells cultures from one laboratory to another for further culturing involves risks and often only a fraction of the cells are viable and can continue propagation in pluripotent state. Currently, there exists no simple solutions for matrix used with cell culture media which would allow propagating stem cells in pluripotent state and which would allow formation and harvesting of cells and cell spheroids without destroying the intercellular network.

The inventors have developed scalable stem cell compositions, culture systems and culturing methods which allow e.g. culturing and propagating pluripotent hESCs in a 3D environment. The invention makes use of cellulose nanofibrils (CNFs), non-animal derived materials with fibre diameter in nanometer range and fibre length in micrometer range, in cell culture matrix. These cellulose nanofibrils are composed of aligned β-D-(1→4)glucopyranose polysaccharide chains[10]. CNFs can be isolated for example from the cell walls of wood, other plants, and certain bacteria. CNFs form hydrogels with tuneable physical and chemical properties[11,12] and diverse pharmaceutical and biomedical applications.

In one aspect is provided a three-dimensional discontinuous entity for culturing of cells comprising an aqueous medium and hydrogel bodies comprising cellulose nanofibrils and/or derivatives thereof suspended in the aqueous medium.

In another aspect is provided a three discontinuous three-dimensional entity and a method for producing such, wherein method for manufacturing a three-dimensional discontinuous entity for culturing cells comprises a. providing cellulose nanofibrils and/or derivatives thereof in a form of i. a homogeneous hydrogel; ii. a combination of the homogeneous hydrogel with an aqueous medium; and/or iii. dehydrated gel bodies or dry granulated cellulose nanofibrils or derivatives thereof hydrated in an aqueous medium; and b. mixing in conditions favouring mechanical disruption of the homogeneous structure of the hydrogel to obtain a suspension of hydrogel bodies as a three-dimensional discontinuous entity.

In another aspect is provided a cell culture matrix and a method for manufacturing such, wherein in the method according to the previous aspects cells are added and the aqueous medium is a cell culture medium.

In one aspect is provided an article and use of the article for cell culture comprising a. a substrate having a surface; b. a three-dimensional discontinuous entity comprising an aqueous medium and hydrogel bodies comprising cellulose nanofibrils and/or derivatives thereof suspended in the aqueous medium, or a three-dimensional discontinuous entity comprising an aqueous medium and hydrogel bodies comprising cellulose nanofibrils and/or derivatives thereof suspended in the aqueous medium in a dehydrated form; c. and optionally at least one component selected from the group consisting of a cell culture medium, extra cellular matrix components, serum, growth factors, proteins, antibiotics, preservatives. Articles comprising the inventive three-dimensional discontinuous entities may be any article suitable for culturing cells, such as cell culture bottles, plates and dishes, multiwall culture plates, microtiter plates, high throughput plates and the like. Preferably, the articles are cell culture grade.

In one aspect is provided use of the three-dimensional discontinuous entity above for culturing cells or tissues.

In one aspect is provided a method of transporting cells, wherein the cells are transported in the three-dimensional discontinuous entity above.

In one aspect is provided a method for three-dimensional or two-dimensional culturing of cells or tissues comprising providing the three-dimensional discontinuous entity above, inoculating at least one cell with the three-dimensional discontinuous entity; and culturing to obtain a cell mass.

In one aspect is provided a kit comprising a first and a second container, the first container comprising the three-dimensional discontinuous entity above or the three-dimensional discontinuous entity above in dehydrated form such as dry powder, concentrated granulate, or concentrated hydrogel body, and the second container comprising cellulase.

DETAILED DESCRIPTION OF THE INVENTION

Figure 1:
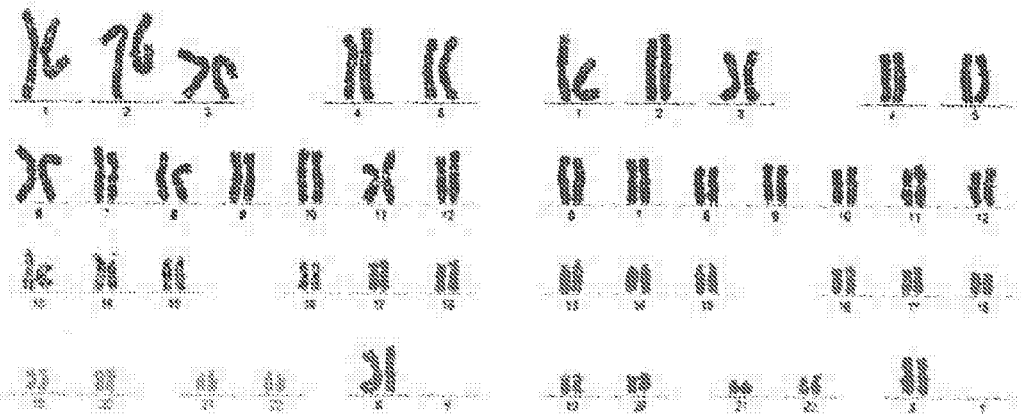
FIG. 1 shows that WA07 and iPS(IMR90)-4 cells have normal karyotype. The cells were first cultured in 3D discontinuous entity of the invention and then transferred to 2D Matrigel platform for karyotyping analysis.

Aspects of the present invention relate to cell culture compositions, three-dimensional discontinuous entities, and to methods of manufacturing and using the same in cell culture and transportation. The cellulose nanofibrils for use according to the present invention can be obtained from non-animal material such as plants or microbes, or derived from bacterial fermentation processes. The compositions and systems may be used to culture cells, such as mammalian embryonic stem cells or induced pluripotent cells. In one aspect the cells may be of human origin. In another aspect the cells can be of non-human origin.

Unless otherwise specified, the terms, which are used in the specification and claims, have the meanings commonly used in the cell culture. Specifically, the following terms have the meanings indicated below.

The term "three-dimensional discontinuous entity" refers to a system having three-dimensionally discontinuous structure. Said entity comprises an aqueous medium and hydrogel bodies comprising cellulose nanofibrils and/or derivatives thereof suspended in the aqueous medium.

"An aqueous medium" refers to any aqueous medium such as water, deionized water, buffer solution, or nutritional medium suitable for maintaining, transporting, isolating, culturing, propagating, passaging or differentiating of cells or tissues. The aqueous medium may further contain various additives such as special extra cellular matrix components, serum, growth factors, antibiotics, preservatives and proteins. As known in the art, the choice of the cell culture media depends on the cell type to be cultured. Many commercial cell culture media exist that support undifferentiated or differentiating growth of cells. Examples of cell culture media suitable in the present invention include mTeSR1 (StemCell Technologies), mesenchymal stem cell media (Lonza, Walkersville, Md., #PT-3001), STEMPRO hESC SFM (Invitrogen), Williams' E (Invitrogen) and differentiation media.

"Discontinuous" refers to the heterogeneous structure of the entity or to interruptions in the physical continuity within the entity, for example interruptions in the aqueous medium by hydrogel bodies or interruptions in and/or between hydrogel bodies by the aqueous medium.

"A hydrogel" or "gel" or "cellulose nanofibril hydrogel" refers to aqueous dispersion of cellulose nanofibrils having a homogeneous and continuous gel structure. The hydrogel can be formed by combining cellulose nanofibrils with e.g. water, buffer solution or cell culture medium or any other aqueous solution optionally supplemented with additives.

"A hydrogel body" and "a hydrogel domain" refer to an aliquot, division, domain, fraction, portion or dose of a hydrogel. The hydrogel body may have a well-defined, indefinite, symmetrical or asymmetrical shape.

"Suspended" or "suspension" when used in context of three-dimensional discontinuous entity or hydrogel bodies refers to a heterogeneous mixture of an aqueous medium and hydrogel wherein the hydrogel may be present as separate or interconnected hydrogel bodies.

"Interconnected" and "interconnection" when used in context of hydrogel bodies refers to a system where the hydrogel bodies are in contact with each other. The contact may be a direct connection between the hydrogel bodies or the hydrogel bodies may be loosely connected. When the homogeneous structure of the hydrogel is broken e.g. by mixing, the resulting discontinuous structure is characterized by hydrogel bodies of different sizes and forms. I one aspect the resulting system may contain aqueous cavities between interconnected gel bodies or the loosely connected hydrogel bodies may "float" in the aqueous medium having contacts with each other. In one aspect the hydrogel bodies may be indirectly connected via e.g. cells or other components present in the system.

The term "cell culture matrix" refers to a system comprising cells and/or tissue and the three-dimensional discontinuous entity, the cells and/or tissue being present at least partially embedded in said entity in a three-dimensional or two-dimensional arrangement. Three-dimensional and two-dimensional in context of cell cultures refers to the way the cells are arranged, for example 3D may refer to cluster or spheroid-like arrangement and 2D to single or layered arrangement.

The term "cell culture" or "culturing of cells" refers to maintaining, transporting, isolating, culturing, propagating, passaging or differentiating of cells or tissues. Cells can be in any arrangement such as individual cells, monolayers, cell clusters or spheroids or as tissue.

The term "cellulose raw material" refers to any cellulose raw material source that can be used in production of cellulose pulp, refined pulp, or cellulose nanofibrils. The raw material can be based on any plant material that contains cellulose. The raw material can also be derived from certain bacterial fermentation processes. Plant material may be wood. Wood can be from softwood tree such as spruce, pine, fir, larch, douglas-fir or hemlock, or from hardwood tree such as birch, aspen, poplar, alder, *eucalyptus* or *acacia*, or from a mixture of softwoods and hardwoods. Non-wood material can be from agricultural residues, grasses or other plant substances such as straw, leaves, bark, seeds, hulls, flowers, vegetables or fruits from cotton, corn, wheat, oat, rye, barley, rice, flax, hemp, manila hemp, sisal hemp, jute, ramie, kenaf, bagasse, bamboo or reed. The cellulose raw material could be also derived from the cellulose-producing micro-organism. The micro-organisms can be of the genus *Acetobacter, Agrobacterium, Rhizobium, Pseudomonas* or *Alcaligenes*, preferably of the genus *Acetobacter* and more preferably of the species *Acetobacter xylinum* or *Acetobacter pasteurianus*.

The term "cellulose pulp" refers to cellulose fibers, which are isolated from any cellulose raw material using chemical, mechanical, thermo mechanical, or chemi thermo mechanical pulping processes. Typically the diameter of the fibers varies between 15-25 μm and length exceeds 500 μm, but the present invention is not intended to be limited to these parameters.

The term "cellulose nanofibril" refers to a collection of isolated cellulose nanofibrils (CNF) or nanofiber bundles derived from cellulose raw material or cellulose pulp. Nanofibrils have typically high aspect ratio: the length might exceed one micrometer while the number-average diameter is typically below 200 nm. The diameter of nanofiber bundles can also be larger but generally less than 1 μm. The smallest nanofibrils are similar to so called elementary fibrils, which are typically 2-12 nm in diameter. The dimensions of the fibrils or fibril bundles are dependent on raw material and disintegration method. The cellulose nanofibrils may also contain some hemicelluloses; the amount is dependent on the plant source. Mechanical disintegration of cellulose nanofibrils from cellulose raw material, cellulose pulp, or refined pulp is carried out with suitable equipment such as a refiner, grinder, homogenizer, colloider, friction grinder, ultrasound sonicator, fluidizer such as microfluidizer, macrofluidizer or fluidizer-type homogenizer. In one aspect the cellulose nanofibrils are derived from plants. "Cellulose nanofibrils" can also be directly isolated from certain fermentation processes. The cellulose-producing micro-organism of the present invention may be of the genus *Acetobacter, Agrobacterium, Rhizobium, Pseudomonas* or *Alcaligenes*, preferably of the genus *Acetobacter* and more preferably of the species *Acetobacter xylinum* or *Acetobacter pasteurianus*. Cellulose nanofibrils are characterized by very high water retention values, a high degree of chemical accessibility and the ability to form stable gels, hydrogels, in water or other polar solvents. Cellulose nanofibril product is typically a dense network of highly fibrillated cellulose.

To obtain cellulose nanofibrils mechanical disintegration of cellulose pulp or oxidized cellulose raw material is carried out with suitable equipment such as a refiner, grinder, homogenizer, colloider, friction grinder, ultrasound-sonicator, fluidizer such as microfluidizer, macrofluidizer or fluidizer-type homogenizer. Preferably mechanically disintegrated cellulose nanofibrils are used.

Several different grades of cellulose nanofibrils have been developed using various production techniques. The grades have different properties depending on the manufacturing method, degree of fibrillation and chemical composition. The chemical compositions of the grades also vary. Depending on the raw material source, e.g. HW vs. SW pulp, different polysaccharide composition exists in the final cellulose nanofibril product. Typically, non-ionic or native grades have wider fibril diameter while the chemically modified grades are much thinner and have a continuous network. The number average fibril diameter of the cellulose nanofibril is suitably from 1 to 200 nm, preferably the number average fibril diameter of native grades is from 1 to 100 nm, and in chemically modified grades from 1 to 20 nm. Size distribution is also narrower for the modified grades. Native ion-exchanged cellulose nanofibrils exhibit discontinuous structure which is partially non-homogenous. For cell culture applications the cellulose nanofibrils are preferably non-toxic to cells.

Derivative of cellulose nanofibril can be any chemically or physically modified derivate of cellulose nanofibrils or nanofiber bundles. The chemical modification could be based for example on carboxymethylation, oxidation, esterification, or etherification reaction of cellulose molecules. Modification could also be realized by physical adsorption of anionic, cationic, or non-ionic substances or any combination of these on cellulose surface. The described modification can be carried out before, after, or during the production of cellulose nanofibrils. Certain modifications may lead to CNF materials that are degradable in human body.

Microbial purity of the cellulose nanofibrils and hydrogels containing them, is essential for the cell culture performance. Therefore, the cellulose nanofibrils may be sterilized prior to cell culture experiments in a hydrogel form. In addition to that it is important to minimize the microbial contamination of the product before and during the fibrillation. Prior to fibrillation, it is advantageous to aseptically collect the cellulose pulp from the pulp mill immediately after bleaching stage when the pulp is still sterile.

There are several widely used synonyms for cellulose nanofibrils. For example: nanocellulose, nanofibrillated cellulose (CNF), nanofibrillar cellulose, cellulose nanofiber, nano-scale fibrillated cellulose, microfibrillar cellulose, microfibrillated cellulose (MFC), or cellulose microfibrils. In addition, cellulose nanofibrils produced by certain microbes has also various synonyms. For example, bacterial cellulose, microbial cellulose (MC), biocellulose, nata de coco (NDC), or coco de nata.

Chemically, cellulose macromolecules are known to be very stable molecules. Hydrolysis of cellulose requires using harsh conditions and typically strong acids, like 56% sulphuric acid, are used.

The dimensions of individual cellulose nanofibrils are close to dimensions of collagen fibers in ECM, i.e. 4-10 nm. Therefore, CNF based hydrogels can be used in 3D cell culture matrix.

In the cell culture experiments of the present invention, two kinds of cellulose nanofibrils were used: native CNF forming opaque hydrogels and chemically modified anionic CNF forming optically transparent hydrogels. Detailed description of the materials is presented in the Examples, Materials and methods section. The concentration of CNF in the hydrogel is adapted to a concentration suitable for the cell which is cultured. The concentration of the CNF in the total volume may vary in the range 0.01-10% (w/v) depending on e.g. the cell type and cell line. In stem cell culturing concentrations in the lower end are typically preferred whereas higher concentrations are typical when differentiated cells, such as liver cells, are cultured. Due to the discontinuous nature of the CNF hydrogel, the total CNF concentration may be different from the local CNF concentration in the three-dimensional discontinuous entity. For pluripotent cells a CNF concentration in the total volume of the three-dimensional discontinuous entity in the range of 0.05-1.5% (w/v) may be used, such as w/v concentrations of 0.05, 0.06%, 0.07%, 0.08%, 0.09%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.05%, 1.1%, 1.15%, 1.2%, 1.25%, 1.3%, 1.35%, 1.4%, 1.45% or 1.5%. The total CNF concentration may also be 1%, 1.5%, 2%, 2.5%, 3%, 3.5%, 4%, 4.5%, 5%, 5.5%, 6%, 6.5%, 7%, 7.5%, 8%, 8.5%, 9%, 9.5, or 10%. It is obvious in view of the structure of the three-dimensional discontinuous entity according to the invention that the CNF concentration above refers to the CNF concentration in the volume of the total three-dimensional discontinuous entity and the local CNF concentrations vary in different parts of the three-dimensional discontinuous entity. To properly understand the nature of the three-dimensional discontinuous entity according to the invention it should be appreciated that in a special case the local concentration of the CNF may be a lot higher than the concentration in the total volume if the hydrogel body completely fills the area of interest. On the other hand, if the area of interest is inside an aqueous cavity surrounded by the discontinuous CNF hydrogel, the local CNF concentration may be 0%. (See FIG. 24).

The fraction volume of the gel bodies comprising the three-dimensional discontinuous entity may vary between 50% and 99% of the total volume of the three-dimensional discontinuous entity and, accordingly, the local CNF concentration may be higher or lower than that of the total entity. The fraction volume of the gel bodies may be for example 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. The fraction of the gel bodies may be qualitatively determined readily e.g. by inspection under microscope or by sedimentation analysis.

The yield strength or yield point refers to the stress at which a material begins to deform plastically. The yield stress may be defined any method known in the art. The yield stress of a single hydrogel body is essentially the same as the yield stress of the homogeneous cellulose nanofiber hydrogel.

The cellulose nanofibrils or a derivative thereof of the present invention can comprise chemically or physically modified derivatives of a cellulose nanofibrils or nanofiber bundles.

The term "cell culture matrix" refers to material configured for cell culturing and providing a growth matrix that increases the available attachment surface for the adherence of the cells so as to mimic the infrastructure of the tissue.

The term "article for cell culture" refers to any article suitable for cell culture including single and multi-well plates, such as 6, 12, 96, 384, and 1536 well plates, jars, petri dishes, flasks, multi-layered flasks, beakers, plates, roller bottles, slides, such as chambered and multichambered culture slides, tubes, cover slips, bags, membranes, hollow fibers, beads and microcarriers, cups, spinner bottles, perfusion chambers, syringes, bioreactors, and fermenters.

"In dehydrated form" refers to form of the material in which some but not necessarily all water is removed from the material in question. Thus, the term dehydrated encompasses e.g. concentrated slurries, granules, flakes, and powders.

The term "kit" refers to a combination of articles or containers that facilitate a method, assay, or manipulation of the three-dimensional discontinuous entity or articles for cell culture using such. Kits can optionally contain instructions describing how to use the kit (e.g., instructions describing the methods of the invention), cartridges, mixing stations, chemical reagents, as well as other components. Kit components may be packaged together in one container (e.g., box, wrapping, and the like) for shipment, storage, or use, or may be packaged in two or more containers.

The present three-dimensional discontinuous entity, cell culture matrix or article may further comprise suitable additives selected from the group consisting of nutrients, buffering agents, pH indicators, extra cellular matrix components, serum, growth factors, antibiotics, preservatives and proteins.

Any cell can be cultured using the present three-dimensional discontinuous entity and cell culture articles. Eukaryotic cells, such as animal cells e.g. mammalian cells, plant cells, algal and fungal cells, can be grown using the three-dimensional discontinuous entity and article, as well as prokaryotic cells such as bacterial cells. In one aspect the cells can be human primary cells from any normal or abnormal tissue type, human secondary cell lines from any tissue type, human immortalized cell lines, and human cancer cells from either primary tumor or metastastic tumor. In one aspect the cells may be any undifferentiated cells, such as pluripotent, multipotent, oligopotent or unipotent cells including embryonic stem cells, non-human embryonic stem cells, induced pluripotent stem cells, somatic multipotent stem cells, somatic pluripotent stem cells, tissue specific stem cells, mesenchymal stem cells, or progenitor cells, neural stem cells, hepatic stem cells, or endothelial stem cells. A suitable cell to be cultured using the present three-dimensional discontinuous entity or article is a human or non-human ESC. A human or non-human iPSC is also suitable. In one aspect the cell to be used in the products according to the invention is any stem cell which is derived from established hES cell lines available to the public or which is obtained by a method which does not exclusively involve destruction of human embryos from which the said product is derived. In one aspect more than one cell type of different origin is cultured as a co-culture.

The present three-dimensional discontinuous entity, article and methods provide culturing of cells for a long time. When undifferentiated cells are cultured, they can be propagated and passaged several times while the pluripotency of the cell mass is maintained. This allows increasing the pluripotent cell mass into larger quantities required e.g. for therapy.

The cells cultured using the present three-dimensional discontinuous entity, article and methods can be transported in the culture system or article without need for freezing the cells before transportation. In the present systems and applications the cultured cells can be transported directly after culturing them in the three-dimensional discontinuous entity or article e.g. at +37° C. without additional steps and culturing of the transported cells can be continued using the same system and apparatus which was used in the transportation. The transported cells can be harvested from the matrix and the culturing may be continued in 2D or 3D culture.

Depending on the cell line and the intended use of the cultured cell, the culturing may be carried out 2D or 3D. The cells are dispersed or inoculated on or in the three-dimensional discontinuous entity or article allowing 2D or 3D growth of cells on the hydrogel bodies and penetration of the propagating cells and extracellular structures of the cultured cells inside the hydrogel bodies.

The removal of cellulose nanofibers can be carried out for example with enzymes mixtures comprising all necessary enzymes for total degradation of cellulose molecules as well as other wood derived components in it, such as hemicelluloses. Proper enzymes are for example designed enzyme mixtures for the CNF in question and commercially available cellulase-hemicellulase preparations. The composition of the mixture can vary depending on the chemical composition of the raw material used for production of that CNF. For example when birch pulp is used for production of CNF the mixture includes at least intact endo- and exocellulases or parts of them, endo-xylanases and β-D-glycosidases and β-D-xylosidases. For hydrolysis of softwood derived CNF the mixture needs to be supplemented at least with endo-mannanases and β-D-mannosidases. The benefit of designed mixtures pooled from purified enzyme components is that they do not contain additional proteins or other unwanted components, such as side activities, debris from the cultivation organism or residues from culture broth, which is often the case for commercial enzyme preparations. Especially harmful is, if the preparation contains proteases, which might attack on the cultured cell surfaces. Commercial enzyme mixtures designated for total hydrolysis of plant based materials can also be used in hydrolysis of CNF, but more preferably after at least crude purification step, such as gel filtration or dialysis. Regardless of the enzyme preparation, either a designed or commercial mixture, the components are selected so that they can optimally hydrolyse CNF for example in respect of pH, temperature and ionic strength. Commercial preparations are available, which are acting either in the acidic pH values (pH 3.5-5) or basic pH values (pH 6-8) and at temperatures from room temperature up to 60-80° C. Very often the cells are grown at 37° C., which is an optimal temperature for the most cellulases and hemicellulases.

The cultured cell lines can be also genetically engineered to produce the needed enzyme protein into the culture system.

Enzymatic degradation of CNF hydrogels was demonstrated by hydrolyzing gravel containing 0.5% hydrogels made by processing from birch pulp with a designed enzyme preparation, which contained (as protein proportions) of 50%, 20%, 13% and 5% of CBH I, CBH II, EG I and EG II cellulases, respectively, and 10% and 2% endo-xylanase and β-D-xylosidase, respectively, as calculated from the total protein content of the mixture. When CNF derived from other raw material is used for cultivation the composition of the mixture is respectively, customised with appropriate enzymes. Celluclast 1.5 LFG, CCN0367 (Novozymes, pH opt 5), Prot. 90 mg/ml. Degradation of native CNF was conducted at pH 5 at 50° C. for 4 days and degradation of transparent CNF at pH 7 at 21° for one hour. Enzyme dosage was 5 mg of enzyme to one gram of CNF.

Enzymatic hydrolysis It is commonly known that certain enzymes, cellulases, are able to hydrolyse [beta]-(1-4)-bonds in cellulose. For example endo-1,4-p-glucanases (EGs) that target cellulose chains in random locations away from the chain ends; exoglucanases or exocellobiohydrolases (CBHs) that degrade cellulose by splitting off molecules from both ends of the chain producing cellobiose dimers; and [beta]-glucosidases (BGLs) that hydrolyze the oligosaccharides produced and cellobiose units (produced during EG and CBH attack) to glucose. Respectively, cellulose nanofibers can be enzymatically hydrolyzed to glucose with an aid of cellulases (Ahola, S., Turon, X., Osterberg, M., Laine, J., Rojas, O. J., Langmuir, 2008, 24, 11592-11599). Total hydrolysis of CNF to monomeric sugars necessitates that the enzyme mixture contains also endo acting hemicellulases, such as xylanases and mannanases, and β-D-glycosidases, β-D-xylosidases and -D-mannosidases. When only partial hydrolysis is aimed, for example to reduce the viscosity of hydrogel, composition of the enzyme mixture can be tuned to include excess endoglucanases and less or no cellobiohydrolases. In the latter case hemicellulases can be included into the mixture since they enhance hydrolytic action of cellulases. Enzymatic hydrolysis of cellulose can be utilized in cellulose nanofiber containing cell culture systems for various reasons. Upon the hydrolysis of CNF hydrogel, the viscosity of the media is drastically lowered and the cultured cell structures are easily accessible e.g. for staining. Also, after the hydrolysis, the cell structures can be transferred or transplanted without the cellulose containing material. The degradation product, glucose, is generally non-toxic to cells and can be utilized as a nutrient in cell culturing.

Figure 14:
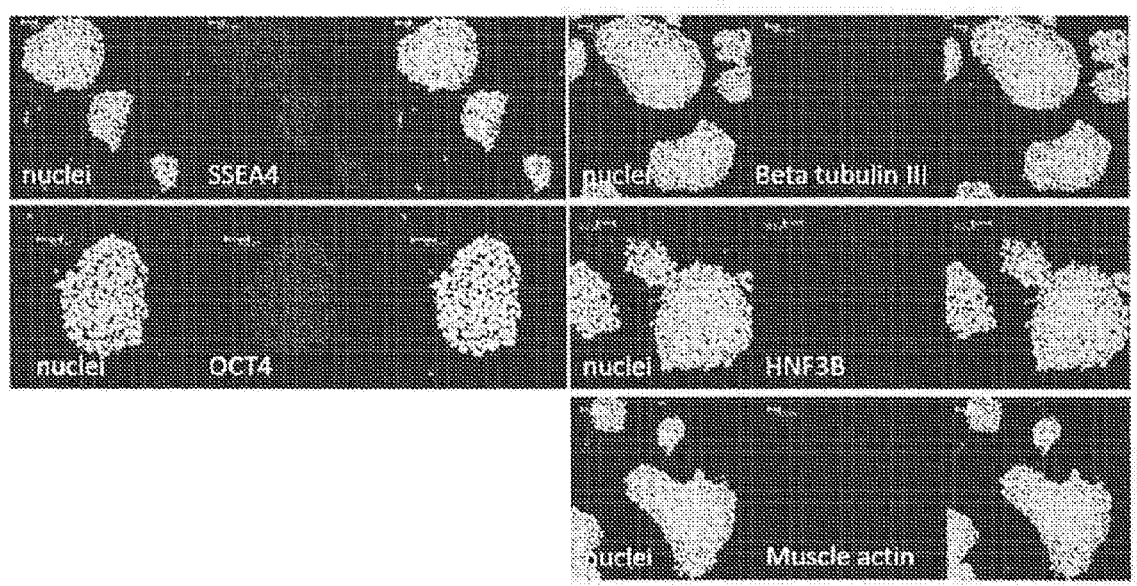
FIG. 14 shows WA07 cells transferred from 3D culture in 3D discontinuous entity of the invention to 2D vitronectin express SSEA4 and OCT4 but not beta-tubulin III, muscle actin and HNF3B. Scale bar: 50 μm.

The enzymatic hydrolysis of cellulose nanofibers can be conducted with an aid of different cellulases at different environment. In FIG. 14, the effect of commercial Celluclast enzymes on the suspending power of the gels is demonstrated. Both native and transparent CNF hydrogels loose the suspending power due to enzymatic degradation of the gel structure. The cultured cell lines can be also genetically engineered to produce the needed enzyme protein into the culture system.

In case enzymatic hydrolysis, such as a cellulase, is used in breaking the CNF hydrogel, the enzyme may be inactivated or removed from the cell culture system. A skilled person is readily able to select any appropriate method to inactivate or remove the enzyme. Examples of suitable methods include inactivation by inhibitors or neutralizing antibodies, and removal of the cellulase by washing, filtration, affinity purification, or any other method which is suitable for the selected application. Inactivation or removal of the enzyme prevents presence of an active enzyme which is able to break the CNF gel structure in case the cells are cultured in a CNF based matrix after the enzyme treatment. Removal of the enzyme may also be required in certain downstream applications of the cultured cells.

Differentiation of cells can be monitored following expression of any marker gene known in the art. For example early or late markers can be used depending e.g. on specific application and the cell type. Table 1 lists examples of markers that can be monitored when using the methods and products according to the invention.

TABLE 1

Cell markers commonly used to identify stem cells and to characterize differentiated cell types

| Marker | Cell type | Tissue type |
|---|---|---|
| Bone-specific alkaline phosphatase | Osteoblast | Bone |
| Hydroxyapatite | Osteoblast | |
| Osteocalcin | Osteoblast | |
| Bone morphogenetic protein receptor | Mesenchymal stem and progenitor cell | Bone marrow and blood |
| CD4 and CD8 | White blood cell | |
| CD34 | Hematopoietic stem cell, satellite, endothelial progenitor | |
| CD34+Sca1+Lin− profile | Mesenchymal stem cell | |
| CD38 | Absent on hematopoietic stem cell | |
| CD44 | Mesenchymal | |
| c-Kit | Hematopoietic stem cell, mesenchymal stem cell | |
| Colony-forming unit (CFU) | Hematopoietic stem cell, mesenchymal stem cell progenitor | |
| Fibroblast colony-forming unit | Bone marrow | |
| Leukocyte common antigen (CD45) | White blood cell | |
| Lineage surface antigen (Lin) | Hematopoietic stem cell, mesenchymal stem cell | |
| Muc-18 (CD146) | Bone marrow fibroblasts, endothelial | |
| Stem cell antigen (Sca-1) | Hematopoietic stem cell, mesenchymal stem cell | |
| Stro-1 antigen | Stromal (mesenchymal) precursor cells, hematopoietic cells | |
| Thy-1 | Hematopoietic stem cell, mesenchymal stem cell | |
| Collagen type II and IV | Chondrocyte | Cartilage |
| Sulfated proteoglycan | Chondrocyte | |
| Fetal liver kinase-1 (Flk1) | Endothelial | Blood vessel |
| Smooth muscle cell-specific myosin heavy chain | Smooth muscle | |
| Vascular endothelial cell cadherin | Smooth muscle | |
| Adipocyte lipid-binding protein | Adipocyte | Fat |
| Fatty acid transporter | Adipocyte | |
| Adipocyte lipid-binding protein | Adipocyte | |
| Albumin | Hepatocyte | Liver |
| B-1 integrin | Hepatocyte | |
| CD133 | Neural stem cell | Nervous system |
| Glial fibrillary acidic protein | Astrocyte | |
| Microtubule-associated protein-2 | Neuron | |
| Myelin basic protein | Oligodendrocyte | |
| Nestin | Neural progenitor | |
| Neural tubulin | Neuron | |
| Neuroflament | Neuron | |
| Noggin | Neuron | |
| O4 | Oligodendrocyte | |
| O1 | Oligodendrocyte | |
| Synaptophysin | Neuron | |
| Tau | Neuron | |
| Cytokeratin 19 | Pancreatic epithelium | Pancreas |
| Glucagon | Pancreatic islet | |
| Insulin | Pancreatic islet | |
| Insulin-promoting factor-1 | Pancreatic islet | |
| Nestin | Pancreatic progenitor | |
| Panceatic polypeptide | Pancreatic islet | |
| SomatostatiAlkaline phosphatasen | Pancreatic islet | |
| Alpha-fetoprotein | Endoderm | |
| GATA-4 | Endoderm | |
| Hepatocyte nuclear factor-4 | Endoderm | |
| Bone morphogenetic protein-4 | Mesoderm | |
| Brachyury | Mesoderm | |
| Cripto | Pluripotent stem cells, cardiomyocyte | |
| Neuronal cell-adhesion molecule | Ectoderm | |
| Pax6 | Ectoderm | |
| Nestin | Ectoderm, neural and pancreatic progenitor | |
| OCT4 | Pluripotent stem cells | |
| SSEA-3 | Pluripotent stem cells | |
| SSEA-4 | Pluripotent stem cells | |
| Telomerase | Pluripotent stem cells | |

Cells may be detected in the culture using any known detection means or dye known in the art.

In aspect 1 the invention provides a three-dimensional discontinuous entity for culturing of cells comprising
a. an aqueous medium; and
b. hydrogel bodies comprising cellulose nanofibrils and/or derivatives thereof suspended in the aqueous medium.

Aspect 2 provides the three-dimensional discontinuous entity according to aspect 1 wherein the ratio of total volume of the hydrogel bodies to total volume of the three-dimensional discontinuous entity is 10%-99% (v/v), preferably 50%-95% (v/v).

Aspect 3 provides the three-dimensional discontinuous entity according to aspect 1 or 2 wherein the hydrogel bodies are interconnected.

Aspect 4 provides the three-dimensional discontinuous entity according to any one of aspects 1-3 wherein the yield stress of the three-dimensional discontinuous entity is lower than the yield stress of the corresponding continuous hydrogel in the same conditions, such as concentration of CNF.

Aspect 5 provides the three-dimensional discontinuous entity according to any one of aspects 1-4 wherein the yield stress of the three-dimensional discontinuous entity is 1-95% of the yield stress of the corresponding continuous hydrogel in the same conditions Aspect 6 provides the three-dimensional discontinuous entity according to any one of aspects 1-5 wherein the cellulose nanofibrils are of plant origin.

Aspect 7 provides the three-dimensional discontinuous entity according to any one of aspects 1-6 wherein the diameter of the cellulose nanofibrils is less than 1 µm, preferably less than 200 nm, more preferably less than 100 nm.

Aspect 8 provides the three-dimensional discontinuous entity according to any one of aspects 1-7 wherein the cellulose nanofibrils comprise native ion-exchanged, chemically modified or physically modified derivatives of cellulose nanofibrils or nanofibril bundles.

Aspect 9 provides the three-dimensional discontinuous entity according to any one of aspects 1-8 wherein the aqueous medium is a cell culture medium comprising at least one nutrient source and at least one component required for sustaining undifferentiated, differentiating or differentiated cell growth.

Aspect 10 provides a method for manufacturing a three-dimensional discontinuous entity for culturing cells comprising:
a. providing cellulose nanofibrils and/or derivatives thereof in a form of
 i. a homogeneous hydrogel;
 ii. a combination of the homogeneous hydrogel with an aqueous medium; and/or
 iii. dehydrated gel bodies hydrated in an aqueous medium; and
b. mixing in conditions favouring mechanical disruption of the homogeneous structure of the hydrogel to obtain a suspension of hydrogel bodies as a three-dimensional discontinuous entity.

Aspect 11 provides the method according to aspect 10 wherein step a. comprises cellulose nanofibrils provided in a form of the combination of the homogeneous hydrogel with an aqueous medium and, optionally, excess of the aqueous medium is removed.

Aspect 12 provides a method for manufacturing a cell culture matrix wherein in the method according to aspect 10 or 11 cells are added and the aqueous medium is a cell culture medium.

Aspect 13 provides a three-dimensional discontinuous entity or a cell culture matrix manufactured using the method according to any one of aspects 10-12.

Aspect 14 provides a cell culture matrix comprising cells and/or tissue and a three-dimensional discontinuous entity according to any one of the aspects 1-9 or 13 wherein the cells and/or tissue are present at least partially embedded in said entity in a three-dimensional or two-dimensional arrangement.

Aspect 15 provides a cell culture matrix according to aspect 14 wherein the cells are differentiated or undifferentiated mammalian cells.

Aspect 16 provides a cell culture matrix according to aspect 14 wherein the cells are undifferentiated stem cells.

Aspect 17 provides the cell culture matrix according to any one of aspects 14-16 wherein the cells are embryonic stem cells or induced pluripotent stem cells.

Aspect 18 provides the cell culture matrix according to any one of aspects 14-17 wherein the cells are human cells or non-human cells.

Aspect 19 provides the cell culture matrix according to aspect 18 wherein the cells are non-human embryonic stem cells or induced pluripotent stem cells.

Aspect 20 provides an article for cell culture comprising
a. a substrate having a surface;
b. a three-dimensional discontinuous entity according to any one of claim 1-9 or 13, or a three-dimensional discontinuous entity according to any one of claim 1-9 or 13 in a dehydrated form;
c. and optionally at least one component selected from the group consisting of a cell culture medium, extra cellular matrix components, serum, growth factors, proteins, antibiotics, preservatives.

Aspect 21 provides use of the three-dimensional discontinuous entity according to any one of aspects 1-9 or 13, or the article according to aspect 20 for culturing cells or tissues.

Aspect 22 provides a method of transporting cells, wherein the cells are transported in the three-dimensional discontinuous entity according to any one of aspects 1-9 or 13, or in the article according to aspect 20.

Aspect 23 provides a method for three-dimensional or two-dimensional culturing of cells or tissues comprising providing the three-dimensional discontinuous entity according to any one of aspects 1-9 or 13, or the article according to aspect 20, inoculating at least one cell with the three-dimensional discontinuous entity; and culturing to obtain a cell mass.

Aspect 24 provides the method according to aspect 23 wherein at least two cell types of different origin are cultured as a co-culture.

Aspect 25 provides the method according to any one of aspects 23-24 wherein the cells form complexes with the hydrogel bodies.

Aspect 26 provides the method according to any one of aspects 23-25 wherein at least one subculture is carried out by passaging the cultured cells at least once during culturing.

Aspect 27 provides the method according to aspect 25 or 26 wherein the passaging comprises cell mass separation from the three-dimensional discontinuous entity wherein the three-dimensional discontinuous entity is treated with an enzyme.

Aspect 28 provides the method according to aspect 27 wherein the three-dimensional discontinuous entity is enzymatically treated with a cellulase for a time sufficient to at least partly release cell mass.

Aspect 29 provide the method according to aspect 28 wherein the cellulase is inactivated or removed from the cell mass after enzymatic treatment.

Aspect 30 provides the method according to any one of aspects 22-29 wherein the cells comprise undifferentiated cells, such as stem cells, and the cells are maintained undifferentiated between passages.

Aspect 31 provides the method according to any one of aspects 22-30 wherein the cell mass or cells are harvested from the cell culture and mixed with the three-dimensional discontinuous entity according to any one of aspects 1-9 or 13 in a medium suitable for maintaining cell growth to provide a three-dimensional culture; and the culture is incubated in conditions and a time sufficient to promote cell propagation whereby spheroids are formed.

Aspect 32 provides the method according to any one of aspects 23-31 comprising differentiating the cells chemically.

Aspect 33 provides the method according to aspect 32 wherein the differentiation comprises formation of embryoid bodies.

Aspect 34 provides the method according to aspect 22-33 wherein the differentiation of the cell is monitored by following a biomarker such as expression of at least one marker selected from the group of genes indicating pluripotency, early differentiation markers, and late differentiation markers.

Aspect 35 provides a kit comprising a first and a second container, the first container comprising the three-dimensional discontinuous entity according to any one of aspects 1-9 or 13, or the three-dimensional discontinuous entity according to any one of aspects 1-9 or 13 in dehydrated form such as dry powder, concentrated granulate, or concentrated hydrogel body, and the second container comprising cellulase.

EXAMPLES

The following examples are given solely for the purpose of illustrating various aspects of the invention and they are not meant to limit the present invention in any way.

Reagents

Dispase solution (1 mg/ml) and mTeSR1 medium were purchased from Stemcell technologies. DMEM-F12 medium, Versene 1:5000, AlamarBlue® reagent, Alexa Fluor 594 and SYTOX Green were purchased from Invitrogen. Matrigel™ Basement membrane matrix growth factor reduced was purchased from BD Biosciences (Bedford, Mass., USA), recombinant human vitronectin from R&D Systems, human recombinant LM-511 and LM-521 from BioLamina (Sundbyberg, Sweden). Cellulose nanofibril (CNF) hydrogel was kindly provided by UPM-Kymmene Corporation (Espoo, Finland) and cellulase by VTT (Turku, Finland). Calcofluor white stain, monoclonal anti-β-tubulin III (T5076), monoclonal anti-α-fetoprotein (A8452) were purchased from Sigma FLUKA, Oct-3/4 antibody (sc-9081) HNF3B (also called FOXA2, sc-6554), control rabbit IgG, mouse IgG and goat IgG from Santa Cruz Biotechnology (Santa Cruz, USA), monoclonal mouse anti-human muscle actin (IS700) from Dako, anti-SSEA-4 from the Developmental Studies Hybridoma Bank, University of Iowa (IA, USA), normal goat and donkey sera from Millipore (Temecula, Calif., USA) and VECTASHEILD mounting medium (Vector Laboratories, Burlingame, Calif., USA). High capacity RNA-to-cDNA kit and fast SYBR Green master mix are from Applied Biosystems. RNeasy Mini kit was purchased from Qiagen.

The colony density of hESCs and hiPSCs in 0.5% w/v CNF hydrogel were five times higher than in 2D Matrigel platform. CNF hydrogel stock solution (1.8% w/v) was diluted in mTeSR1 medium and mixed with stem cell colonies. The same amount of mTeSR1 medium was added on top of the cell-hydrogel mixture. The medium was renewed daily.

Native cellulose nanofibrils were produced by high pressure homogenization (five subsequent cycles) of highly purified bleached birch pulp, followed by autoclave sterilization. After fluidization, the cellulose nanofibrils were in a form of a dilute hydrogel (2 wt %). Ion-exchanged native cellulose nanofibrils were obtained in a similar manner but additionally prior to fibrillation it was subjected to acid-base treatment in order to remove high valency cations (method described in previous sections). After high pressure homogenization (15 subsequent cycles) the ion-exchanged cellulose nanofibrils form a strong hydrogel having lower turbidity compared to the other sample. Cellulose nanofibrils were sterilized by autoclaving when necessary. Transparent anionic fibril cellulose was obtained as hydrogel (2 wt %) by similar homogenization process of a chemically modified cellulose pulp (TEMPO-oxidized cellulose pulp).

Hydrogel Structure

Cellulose nanofibers are typically very hydrophilic objects due to hydroxyl groups in the glucoside rings and partially charged hemicellulose moieties. Thus, the fibrils form hydrogel structures when dispersed in water at concentrations higher than the overlapping concentration, i.e. typically 0.05-0.2% w/v. The gel structure is highly dependent on shear history of the sample: either continuous or discontinuous structures can be achieved depending on the mixing method after dilution.

The three-dimensional discontinuous entity is obtainable by a method comprising steps of providing cellulose nanofibrils and/or derivatives thereof; mixing said cellulose nanofibrils and/or derivatives thereof with a first aqueous medium to obtain a hydrogel, and mixing said hydrogel with a second aqueous medium to obtain a suspension of hydrogel bodies in the second aqueous medium. The first and the second aqueous medium can be of same medium type, but also different, the first medium being e.g. water and the second cell culture medium. The three-dimensional discontinuous entities can be made also from concentrated cellulose nanofibril hydrogels or from dry cellulose nanofibrils by granulating the concentrated hydrogel or dry cellulose nanofibrils to obtain granules, hydrating the granules in an aqueous medium, and mixing the hydrated granules, optionally adding aqueous medium, to obtain a suspension of hydrogel bodies. The discontinuous structure of the hydrogel can be verified e.g. by simple microscopic analysis or yield stress determination and comparison with the homogeneous hydrogel having the corresponding CNF concentration.

Figure 17:
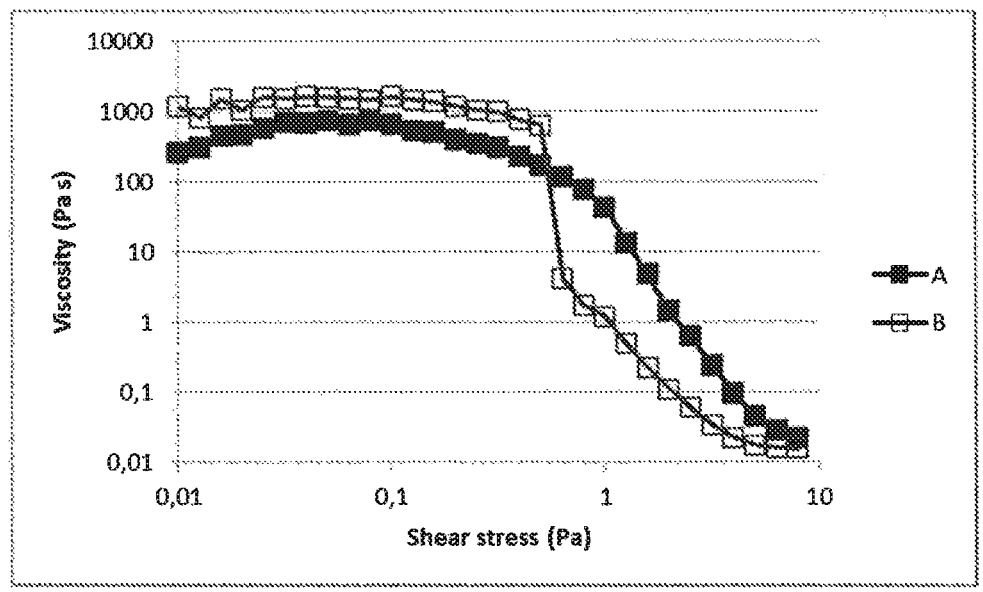
FIG. 17 shows flow profiles of continuous hydrogel structure (A) and 3D discontinuous entity of the invention (B). Ion exchanged native cellulose nanofibrils at 0.5% w/v in aqueous system were used for both A and B.
Figure 18:
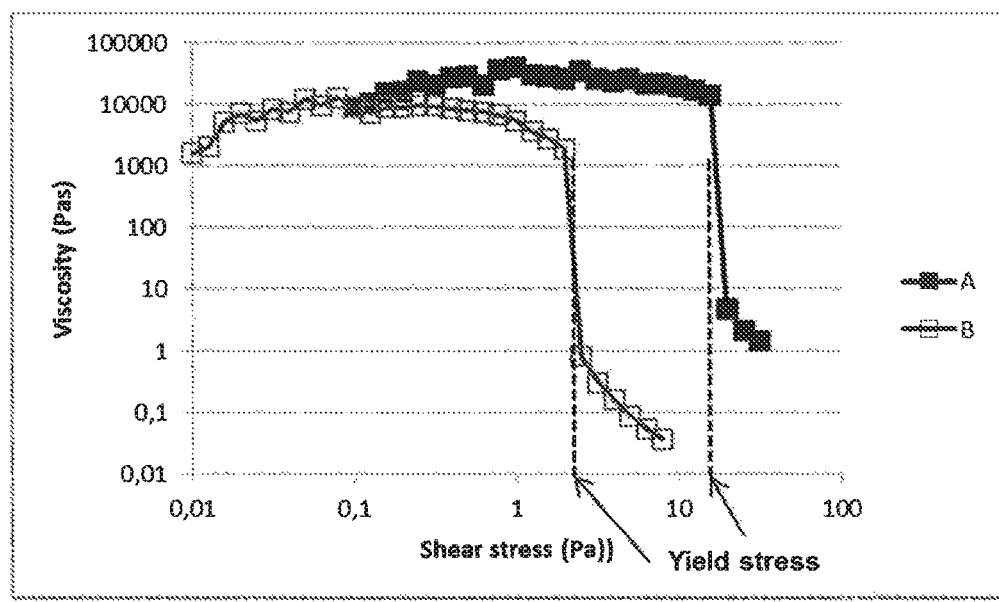
FIG. 18 shows flow profiles of continuous hydrogel structure (A) and 3D discontinuous entity of the invention (B). Anionically modified cellulose nanofibrils at 0.5% w/v in aqueous system were used for both A and B.

Typical for homogeneous and continuous gel structures is high yield stress even at low concentrations. Respectively, discontinuous gel structures have typically lower yield stress value when compared to well activated cases even at the same concentration. This difference is shown in flow profiles in FIGS. 17 and 18 for two kinds of cellulose nanofiber hydrogels at 0.5% w/v. The samples have been diluted from homogeneous 2% gel sample, followed by mixing. FIG. 17 shows the flow profile for the ion exchanged native cellulose nanofibers where the gel structure has been well homogenized after dilution from 2% to 0.5% with a high speed blender to continuous gel structure (curve A). In FIG. 17, also the flow profile of a discontinuous gel structure is shown (curve B). Clearly, the yield stress is lower for discontinuous gel sample, i.e. case (B). Discontinuous gel structure was made by using only weak mixing method after diluting the sample from 2% to 0.5%, for example magnetic stirring or pipetting. Similar observations can be made also for chemically modified cellulose nanofiber hydrogels. FIG. 18 shows the corresponding flow profiles for anionically modified nanofibers dispersed in water at 0.5% w/v for continuous (A) and discontinuous hydrogels (B).

Ion-exchanged native fibril cellulose was obtained in a similar manner but additionally prior to fibrillation it was subjected to acid-base treatment in order to remove high valency cations (method described in previous sections). After high pressure homogenization (15 subsequent cycles) the ion-exchanged fibril cellulose forms a strong hydrogel having lower turbidity compared to the other sample. Cellulose nanofibrils were sterilized by autoclaving when necessary. Transparent anionically modified cellulose nanofibrils were obtained as hydrogel (0.9 wt %) by similar homogenization process of an oxidized cellulose pulp.

The hydrogel samples were diluted from homogeneous 2% gel sample, followed by activation or mixing. FIG. 17 shows the flow profile for the ion exchanged native cellulose nanofibrils where the gel structure has been well homogenized after dilution from 2% to 0.5% with a high speed blender to continuous gel structure (curve A). In FIG. 17, also the flow profile of a discontinuous gel structure of the three-dimensional discontinuous entity is shown (curve B). Clearly, the yield stress is lower for discontinuous gel sample, i.e. case (B). Discontinuous gel structure was made by using only weak activation method after diluting the sample from 2% to 0.5%, for example magnetic stirring or pipetting. Similar observations can be made also for chemically modified cellulose nanofibril hydrogels. FIG. 18 shows the corresponding flow profiles for anionically modified nanofibrils dispersed in water at 0.5% w/v for continuous (A) and discontinuous hydrogels (B).

Figure 19:
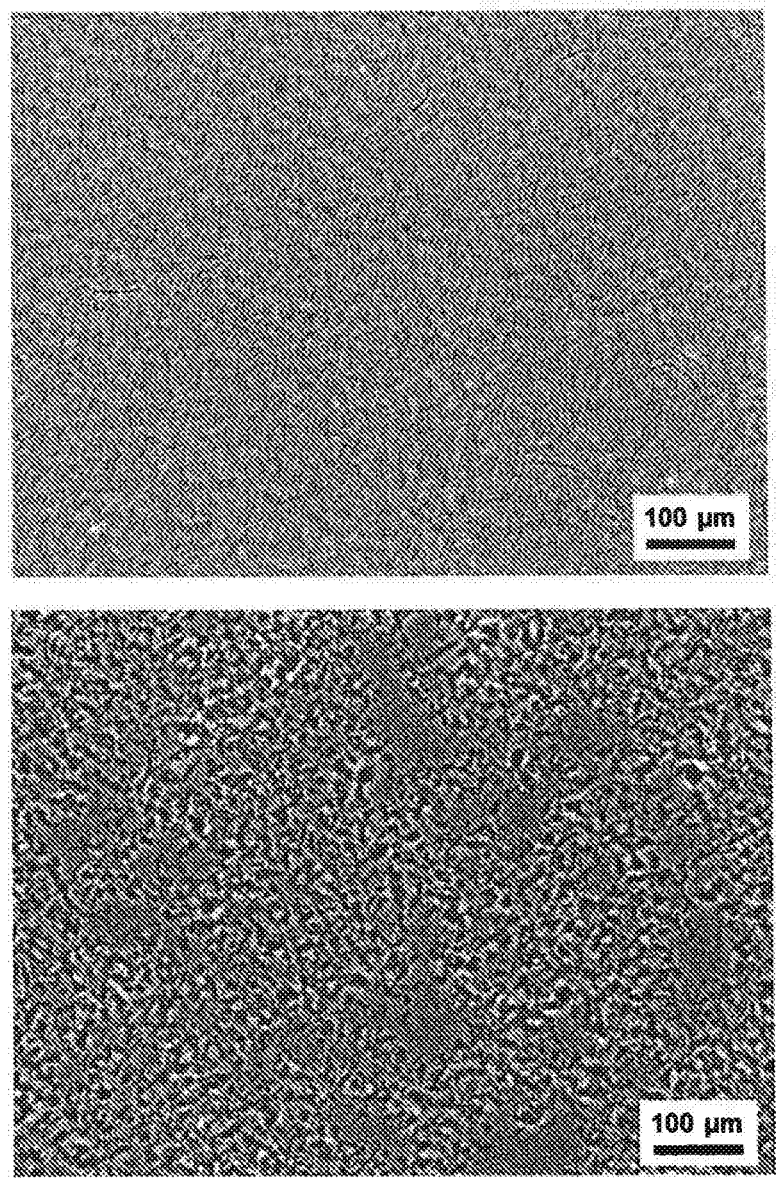
FIG. 19 shows phase contrast optical microscopy images of continuous gel structure (top) and discontinuous (bottom) for the ion exchanged native cellulose nanofibers dispersed in water at 0.5% w/v. Discontinuous gel structure is made by diluting 2% gel sample to 0.5% followed by mixing with five times with a pipette (in 50 mL vial, with 3 mL Pasteur pipette, diameter 0.2 cm).
Figure 23:
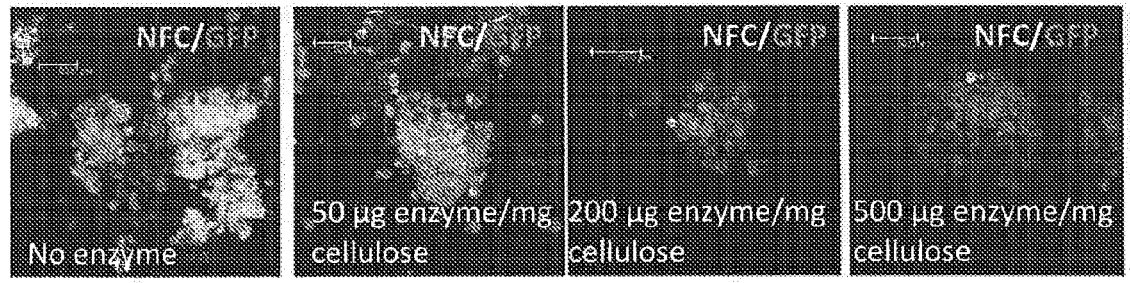
FIG. 23. CNF staining and live cells imaging using a confocal microscope. H9-GFP cells, shown in green, were cultured in 3D discontinuous entity of the invention, the CNF therein is shown in blue. After cellulase treatment, the blue staining was reduced in a concentration-dependent manner. Scale bar: 50 μm FIG. 24. Schematic drawing of different 3D discontinuous hydrogel entities made of cellulose nanofibrils.

The difference in gel structures can visualized also from light microscopy images. FIG. 19 shows the differences of the gel structures for continuous (top) and discontinuous structures (bottom) of the ion exchanged native cellulose nanofibers dispersed in water. In the discontinuous gel structure, voids between the nanofiber phases are well visible. At 0.5% w/v dispersion, the water rich cavities are typically 10-200 micrometers in diameter. The discontinuous structure can be seen also from cell culture microscopy images, FIG. 23, where cellulose nanofibers are forming aggregated areas around the cells.

The relative distribution of the voids, and the actual size, is dependent on starting concentration, total concentration, and method of mixing. For example, if the total concentration of is lower than the gel concentration (typically below 0.05-0.2% w/v) the cellulose nanofibers form gel flock entities that are loosely in contact to each other with certain water containing cavities. If the total concentration is higher than gel concentration of a homogeneous gel, the voids form porous structures described in FIG. 19 if excess water or medium is dispersed carefully into the system. The porosity can be adjusted by altering the strength of the gel domains, i.e. increasing concentration in the areas where the fibrils are present and mixing variable amounts of excess water/medium into the structure.

Figure 20:
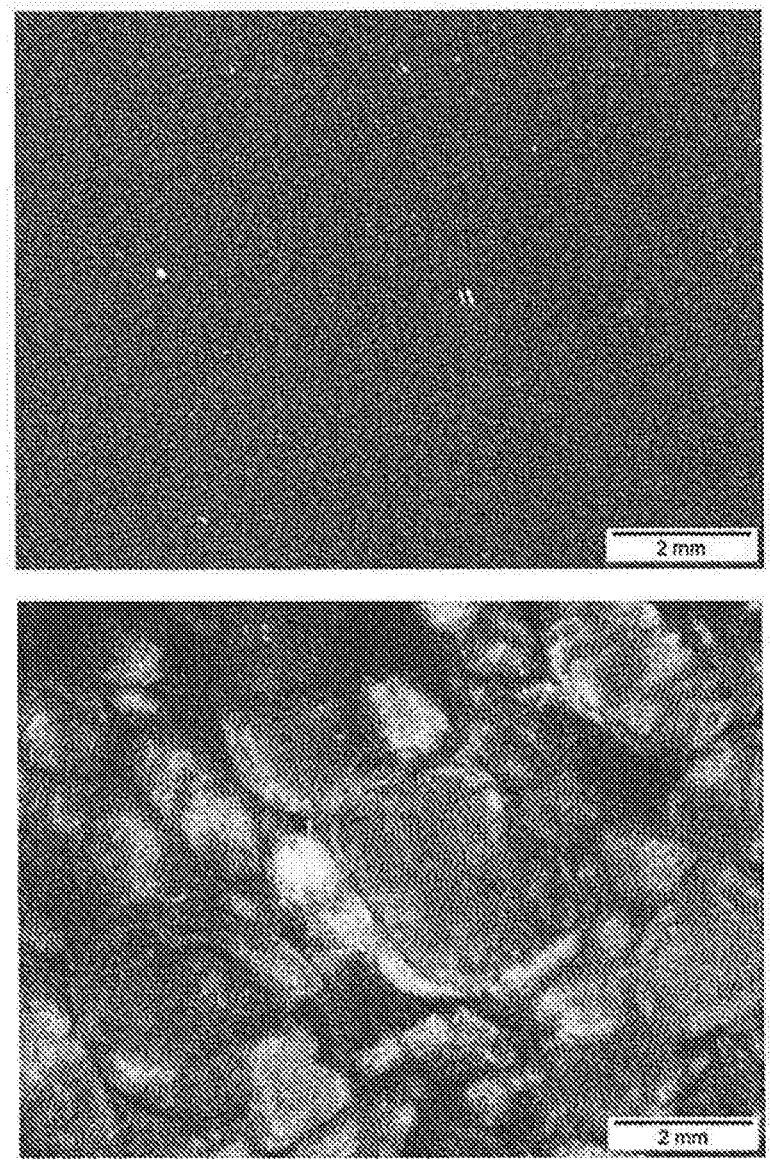
FIG. 20 shows stereo microscopy images of continuous gel structure (top) and discontinuous (bottom) for the anionically modified cellulose nanofibers dispersed in water at 0.5% w/v. Discontinuous gel structure is made by diluting 1-3 mm sized 27% w/v sample to 0.5% followed by mixing with magnetic stirrer (400 ml decanter glass, 5 minutes, 300 rpm).

Discontinuous gel structures can be made also from concentrated (e.g. 10-30% w/v) or even from dry cellulose nanofiber samples. When using dry or concentrated materials, the sample is first granulated to an appropriate size (e.g. 0.1-2 mm), hydrated in water or in cell culture medium, and then activated into either continuous or discontinuous form using appropriate methods. Spray dried particles, size 2-20 micrometers, can be also used as a starting material. The controlled porosity in these kinds of discontinuous gels is dependent on particle size and the total concentration, i.e. distance between the swollen gel domains or gel bodies, see FIGS. 20 and 24.

Figure 24:
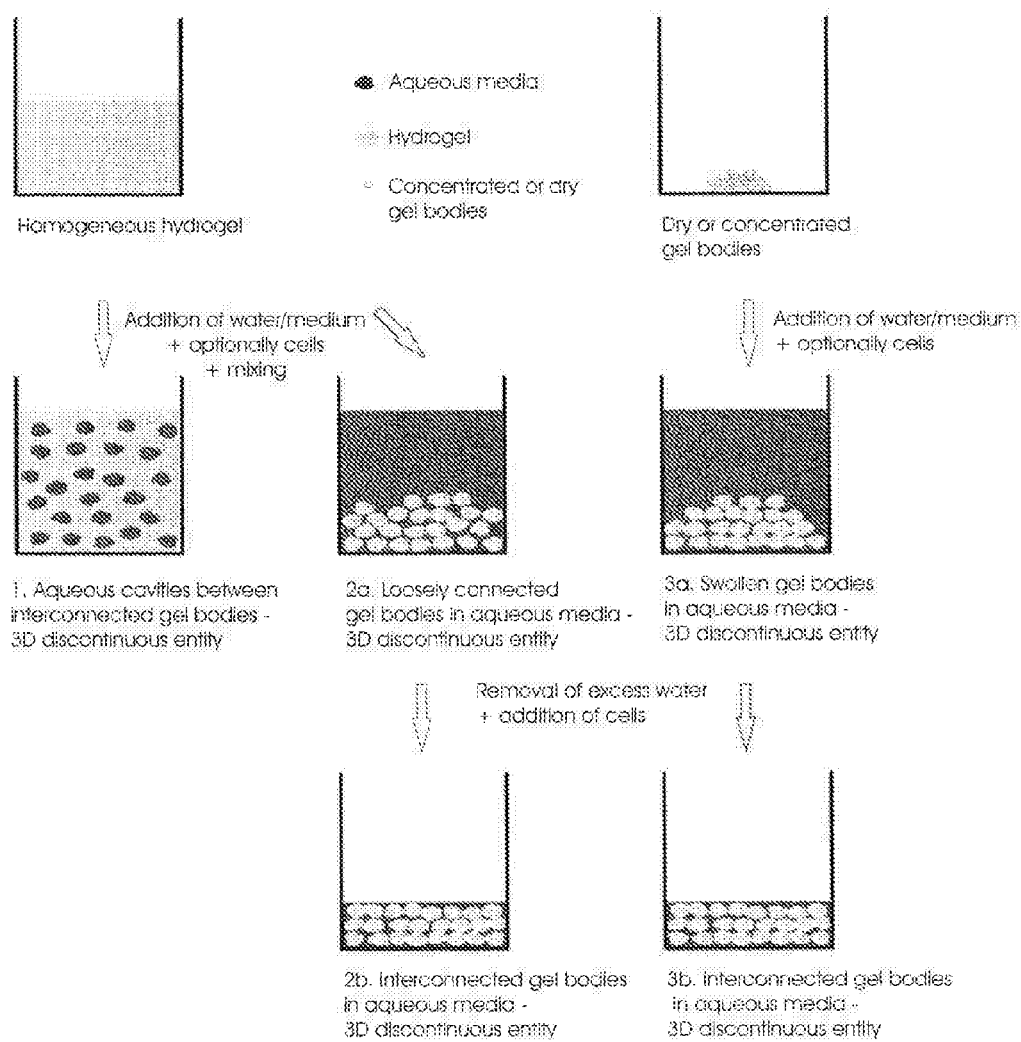
Figure 25:
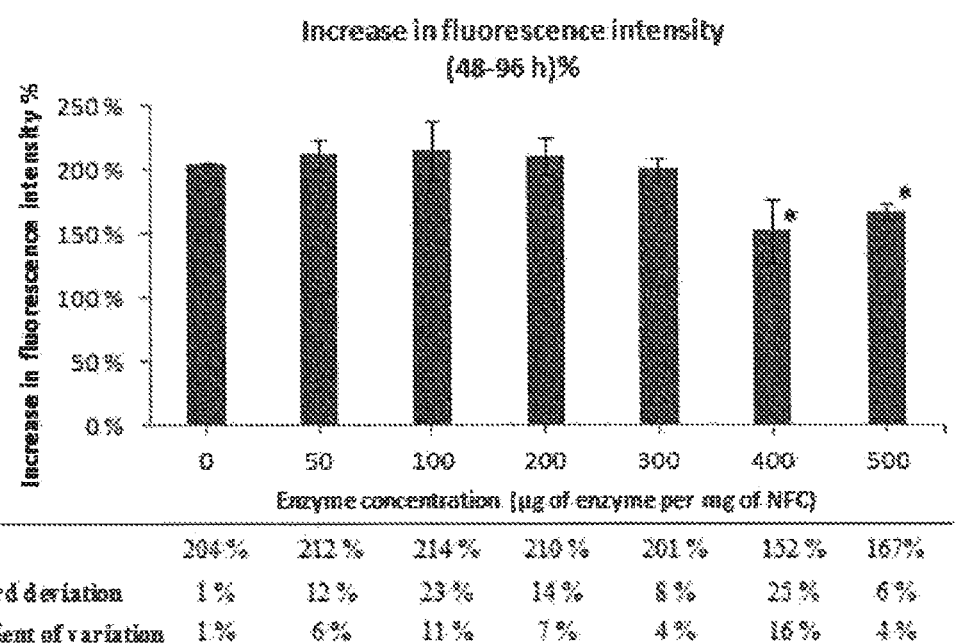
FIG. 25. Mitochondrial metabolic activity of H9-GFP cells treated with cellulase. H9-GFP cells cultured on Matrigel platform were treated with cellulase at 0, 50, 100, 200, 300, 400 and 500 μg/mg of FIG. 25. Mitochondrial metabolic activity of H9-GFP cells treated with cellulase. H9-GFP cells cultured on Matrigel platform were treated with cellulase at 0, 50, 100, 200, 300, 400 and 500 μg/mg of CNF for 24 hours at 37° C. The relative mitochondrial metabolic activity was determined by AlamarBlue® assay one day before and one day after the enzyme treatment. The average increases in fluorescence intensities were calculated from three independent experiments in which six parallel samples for each condition were prepared. The results are expressed as mean±SD (n=3). CNF for 24 hours at 37° C. The relative mitochondrial metabolic activity was determined by AlamarBlue® assay one day before and one day after the enzyme treatment. The average increases in fluorescence intensities were calculated from three independent experiments in which six parallel samples for each condition were prepared. The results are expressed as mean±SD (n=3).

Examples of suitable processes for above mentioned structures have been schematically described in FIG. 24. Case 1 corresponds to the situation visualized also in FIG. 19: discontinuous gel structure is made by diluting homogeneous hydrogel with water/medium with a method that generates water rich cavities into the hydrogel. Cells can be incorporated during or after the dilution and mixing stage. Case 2 describes the situation where the relative volume of water/medium is higher than in the case 1. Higher water fraction leads to loosely connected gel particles. Cells can be incorporated either during or after the dilution and mixing state. The excess water/medium can be removed if needed for example by gentle centrifugation cycle or decantation or filtration (case 2b). Cells can be introduced also in this stage. Case 3 describes the process where the desired structure is made from concentrated NFC gel granulates or even from dry particles. Typically the dry or concentrated particles are first hydrated with water/medium (3a) followed by optional removal of excess water (3b). The cells can be introduced during or after the hydration stage or after the optional water removal stage. The excess water can be removed for example by centrifugation or decanting or filtration. Cases 2 and 3 are visualized in the microscopy image in FIG. 20.

Example 1

Subculture of hPSCs in 0.5% CNF Hydrogel and Recovery of 3D Culture to 2D Platforms To subculture of 3D hPSCs and to recover spheroids from 3D hydrogel to 2D platforms, cellulase was used. Before cellulase treatment, the mTeSR1 medium was removed and the enzyme diluted in fresh mTeSR1 medium was added and incubated with cell-hydrogel mixture at 37° C. for 24 hours.

Figure 2:
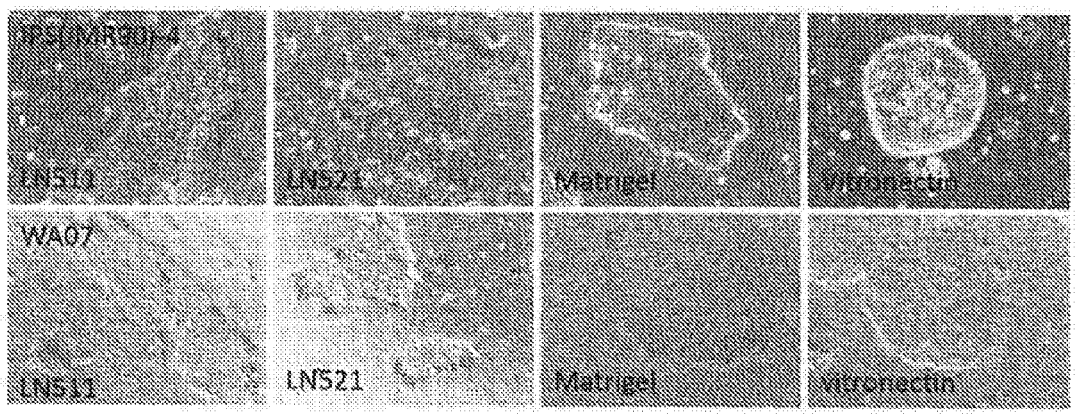
FIG. 2 shows WA07 and iPS(IMR90)-4 cells transferred from 3D culture in 3D discontinuous entity of the invention to 2D Laminin 511-coated, Laminin 521-coated, vitronectin-coated and Matrigel coated dishes show typical stem cell morphology. Magnification: 10×.
Figure 5:
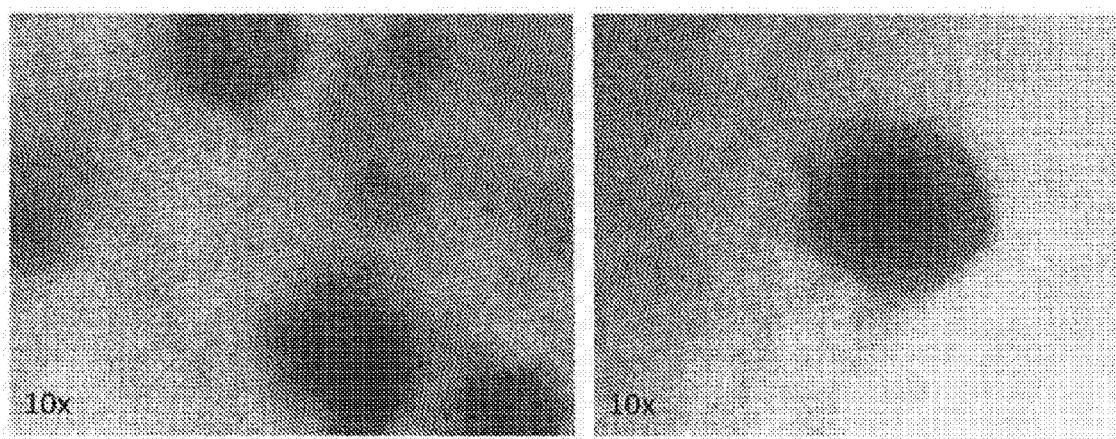
FIG. 5 shows that iPS(IMR90)-4 cells subcultured from 3D culture to new 3D culture in 3D discontinuous entity of the invention were able to form spheroids.

Once the CNF was removed by enzymatic treatment, stem cell spheroids were collected by 100 μm cell strainer to remove cellulase and then treated with Versene 1:5000 for 7 min to reduce their size. For subculture, the smaller cell colonies were mixed with 0.5% w/v CNF hydrogel as described above (FIG. 5). To transfer cells to 2D platforms, the smaller cell colonies were seeded on four different coatings: Matrigel, VN, LM-511 and LM-521. Matrigel coating was prepared as usual. LM-511 and LM-521 coatings were prepared by incubating protein solutions (20 μg/ml LM-511 or 20 μg/ml LM-521) at 37° C. for 2 hours and then 4° C. overnight. VN coating was prepared by incubating 5 μg/ml VN at 4° C. overnight (FIG. 2).

Example 2

Mitochondrial Metabolic Activity

Figure 4:
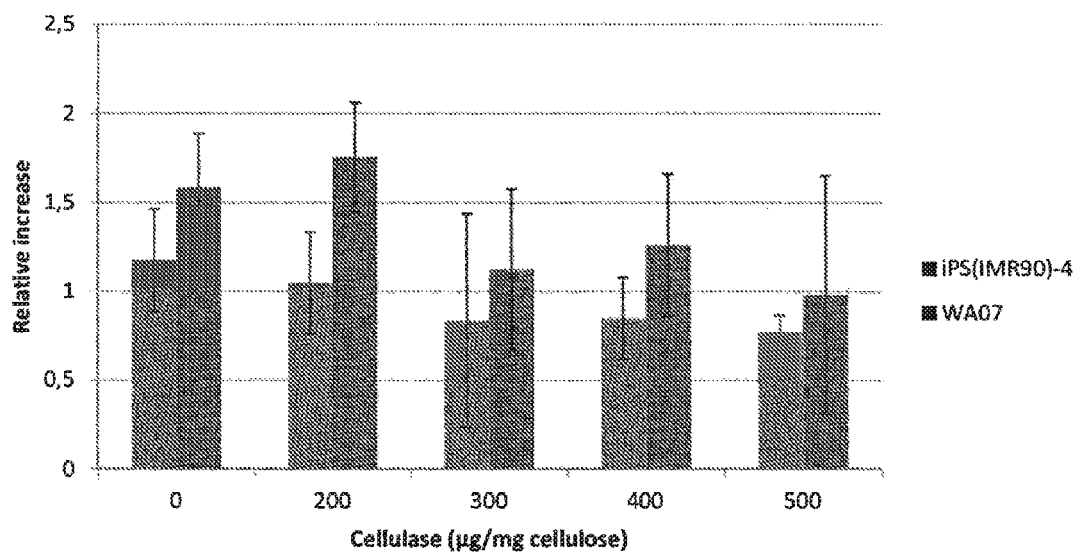
FIG. 4 shows cellulase concentration optimization: 200 μg cellulase/mg cellulose seems to be nontoxic. 300-500 μg cellulase/mg cellulose has minimal negative effect on cell viability. Cell proliferation and viability were monitored by AlarmaBlue assay.

AlamarBlue® reagent was used to measure mitochondrial metabolic activity of stem cells before and after enzymatic treatment in order to select the nontoxic enzyme concentration (FIG. 4). Before and after treatment with various concentrations of cellulose enzyme, 2.5% AlamarBlue® reagent was also used during cell culture in 0.5% w/v CNF hydrogel. AlamarBlue® reagent was added into mTeSR1 medium and incubated with cells at 37° C. for 24 hours. The fluorescence of the AlamarBlue® metabolite was measured at excitation wavelength of 570 nm and emission wavelength of 585 nm by Varioskan Flash spectral scanning multimode reader 2.4.2 (Thermo Scientific).

Example 3

CNF Staining and Live Cells Imaging Using a Confocal Microscope

Figure 3:
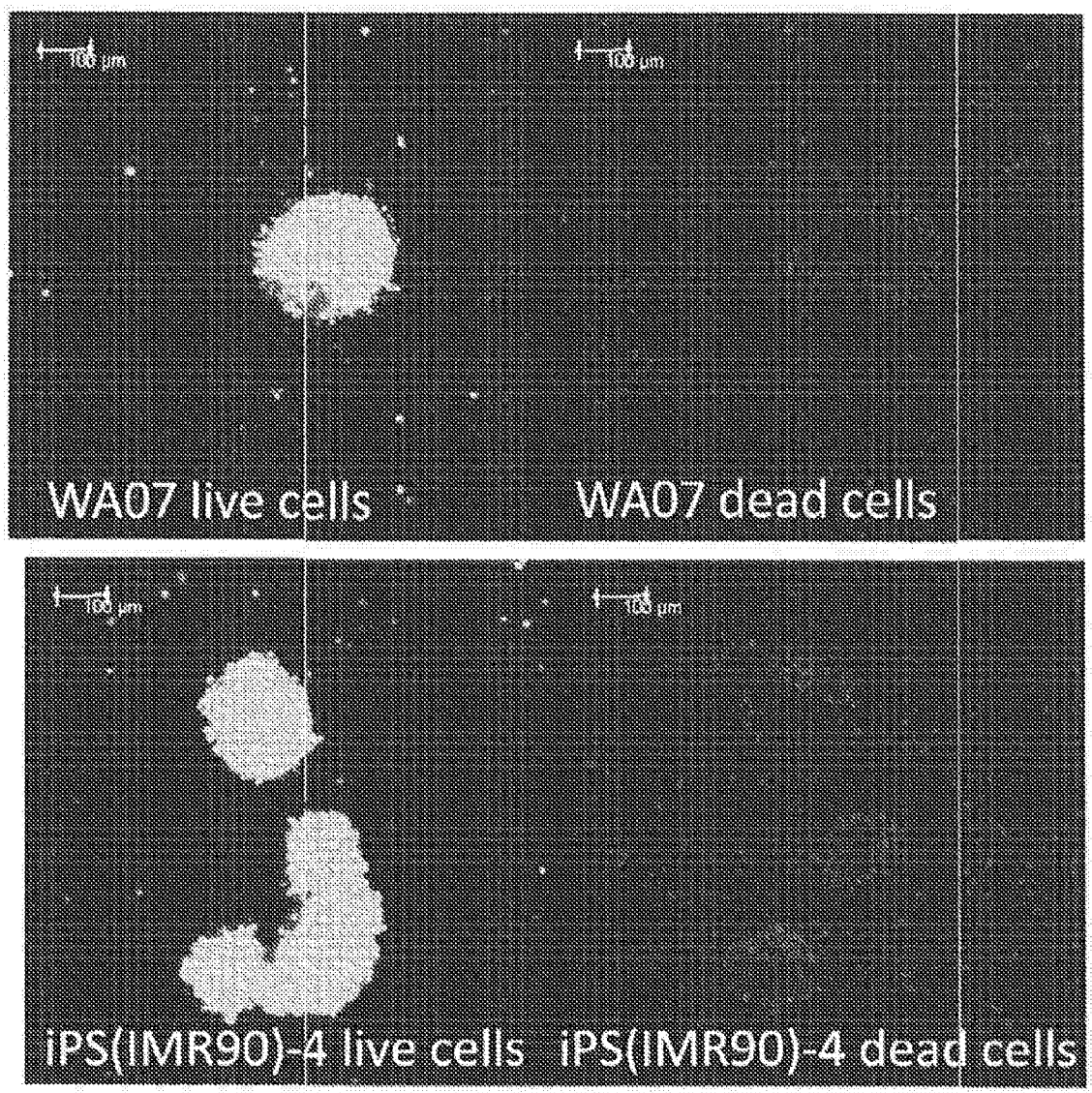
FIG. 3 shows live/dead staining of WA07 and iPS (IMR90)-4 cells cultured for 9 days in 3D discontinuous entity of the invention obtained by diluting and mixing 2% w/v cellulose nanofibril hydrogel to 0.5% w/v: most cells in the clusters are alive (in green) and single cells on the bottom of the well appear to be dead (in red). Scale bar: 100 μm.

To evaluate the enzymatic removal of CNF, calcofluor white stain was added into the culture to stain cellulose. GFP fluorescence of the live cells and stained CNF were visualized under a Leica TCS SP5II HCS A confocal microscope using Argon 488 nm and UV 405 nm lasers, respectively at 37° C. 5% $CO_2$. (FIG. 3)

Example 4

Immunostaining

Figure 21:
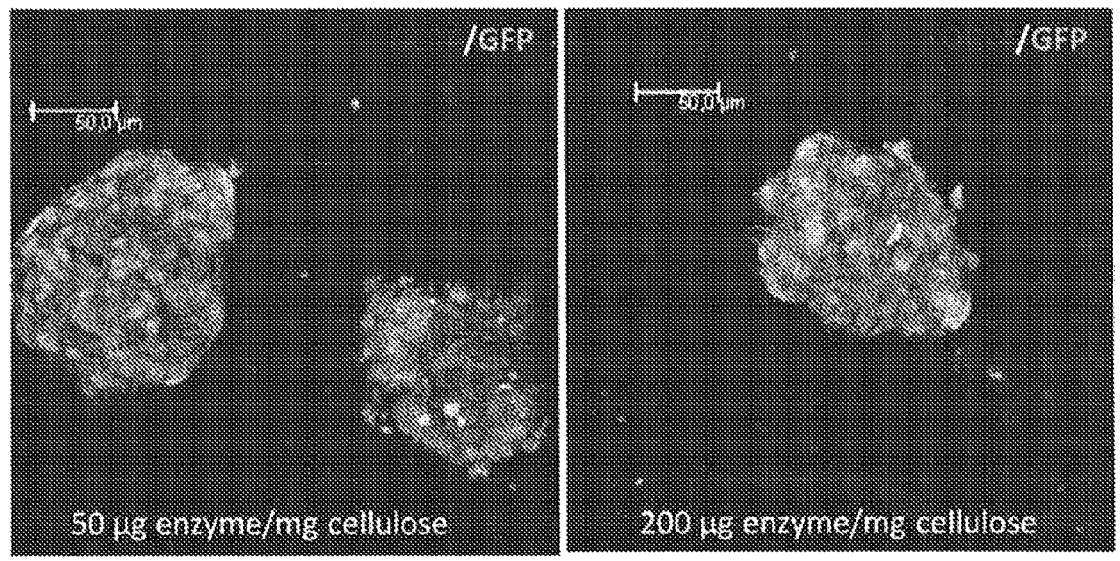
FIG. 21. H9-GFP cells cultured in 3D discontinuous entity of the invention show strong OCT4 staining. OCT4 expression was not compromised by cellulase treatment. Cells are shown in green and OCT4 is stained in red. Scale bar: 50 μm.
Figure 22:
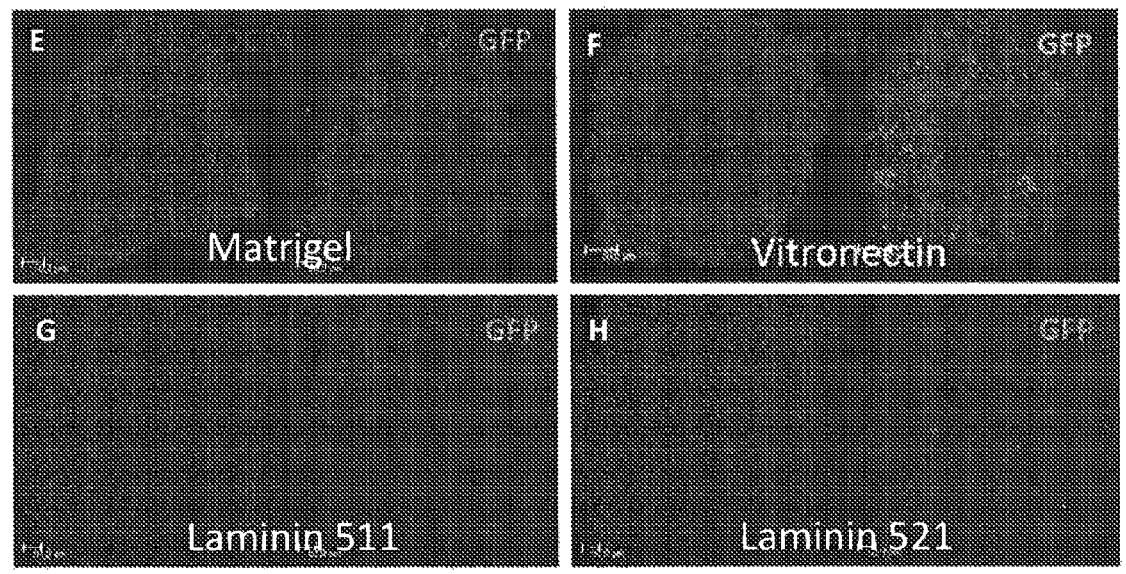
FIG. 22. H9-GFP cells were first cultured in 3D discontinuous entity of the invention and then transferred on 2D Laminin 511-coated, Laminin 521-coated, vitronentin-coated and Matrigel-coated dished. Cells appear in green and OCT4 is stained in red. Scale bar: 50 μm.

Stem cells cultured either in CNF hydrogel (FIG. 21) or on different protein-coated wells (FIGS. 7-14, 22) were fixed with 3.7% paraformaldehyde for 10-30 min at room temperature and thereafter permeabilized with 0.1% Triton X-100 or 0.5% saponin for 10-30 min. After blocking with 10% normal goat or donkey serum, cells were incubated with anti-Oct-3/4, anti-SSEA-4, anti-β-tubulin isotype III, anti-muscle actin, anti-FOXA2 at 4° C. overnight. Negative control samples incubated with control rabbit IgG, mouse IgG or goat IgG were prepared in parallel. The secondary antibody either goat-anti-rabbit Alexa Fluor 594, goat-anti-mouse Alexa Fluor 594 or donkey-anti-goat Alexa Fluor 594 at a dilution of 1:400 was used at room temperature for one hour (2D) or six hours (3D). All washings using PBS-0.2% Tween 20 were repeated three times, 5 min each. After immunostaining, nuclei were stained with SYTOX Green. Cells were then mounted with VECTASHEILD mounting medium. Stainings were viewed under a Leica TCS SP5II HCS A confocal microscope using Argon 488 nm laser for GFP and SYTOX Green and DPSS 561 nm laser for Alexa Fluor 594. The confocal images were analyzed with Imaris 7.4 software (Bitplane AG, Zurich, Switzerland).

Example 5

RNA Extraction and Real-Time Quantitative PCR

Figure 16:
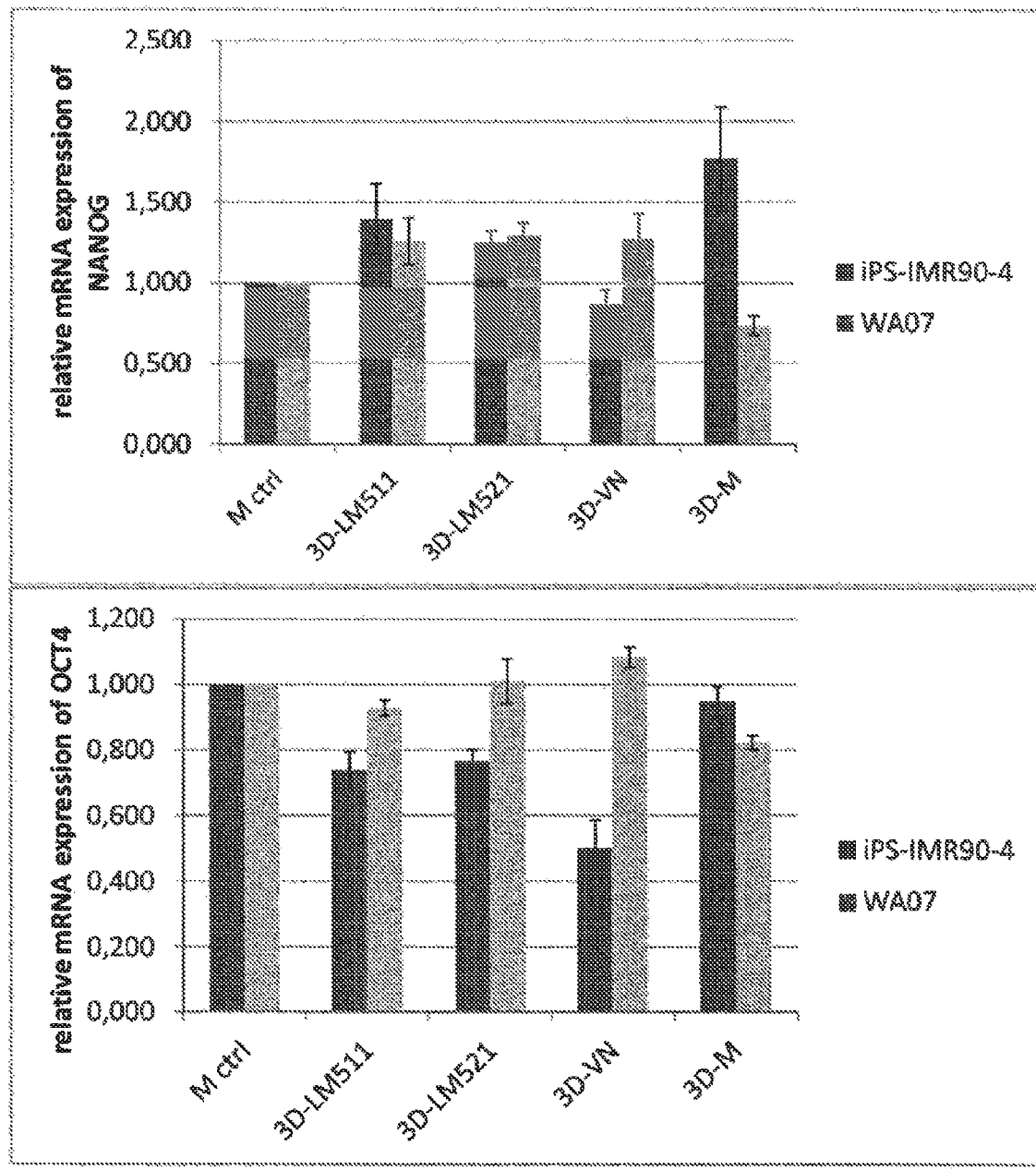
FIG. 16 real-time RT-PCR shows that WA07 and iPS (IMR90)-4 cells transferred from 3D culture in 3D discontinuous entity of the invention to four 2D plateforms (LM511: laminin-511; LM521: laminin-521; VN: vitronectin; M: Matrigel) express similar level of NANOG and OCT4 as those cultured in conventional Matrigel platform (M ctrl) (n=3).

Total RNA was extracted using RNeasy Mini kit (Qiagen GmbH, Hilden, Germany) following the manufacturer's instructions. RNA samples were quantified using a Nano-Drop 2000 spectrophotometer (Thermo Fisher Scientific, Wilmington, Del., USA). All the RNA samples were converted into cDNA at the same experiment to ensure the same reverse transcription efficiency. The cDNA synthesis was performed by using High Capacity RNA-to-cDNA kit (Applied Biosystems, Foster City, Calif., USA). All the cDNA samples were analyzed in duplicate using a Fast SYBR Green Master Mix (Applied Biosystems, Foster City, Calif., USA) on a StepOnePlus Real-Time PCR System (Applied Biosystems, Foster City, Calif., USA). For each gene, a standard curve was generated for OCT4 and NANOG. PCR product quality was monitored using post-PCR dissociation curve analysis (FIG. 16). All primers were synthesized by Oligomer Oy, Finland. The housekeeping gene RPLPO was used as an endogenous control. The PCR cycling conditions were: 40 cycles of 3 s at 95° C. and 30 s annealing/extension at 60° C. The primer sequences were shown in Table 2.

TABLE 2

Primer sequences

| Gene name | ID | Sequences | Amplicon | Comment |
|---|---|---|---|---|
| RPLPO | NM_053275.3 | Forward, SEQ ID NO: 1: AATCTCCAGG GGCACCATT Reverse, SEQ ID NO: 2: CGCTGGCTCC CACTTTGT | 74 bp | Designed by Primer Express |
| NANOG | NM_024865.2 | Forward, SEQ ID NO: 3: GCAGAAGGCC TCAGCACCTA Reverse, SEQ ID NO 4: GGTTCCCAGTCG GGTTCAC | 80 bp | Designed by Primer Express |
| OCT4 | NM_002701.4 | Forward SEQ ID NO: 5: CAGTGCCCGAAAC CCACAC Reverse SEQ ID NO: 6: GGAGACCCAGCAG CCTCAAA | 161 bp | 1 |

Reference:
1. Yu, J. et al. Induced pluripotent stem cell lines derived from human somatic cells. Science 318, 1917-1920 (2007).

Example 6

Karyotyping

For karyotyping analyses, cell colonies were recovered from hydrogel to Matrigel-coated dishes following the above-mentioned procedure. Chromosomal G-band analyses were performed at the Yhtyneet Medix laboratoriot, Finland. Normal karyotype was observed in all cells tested (WA07 and iPS-IMR91-4) (FIG. 1).

Example 7

Embryoid Body Formation

Figure 6:
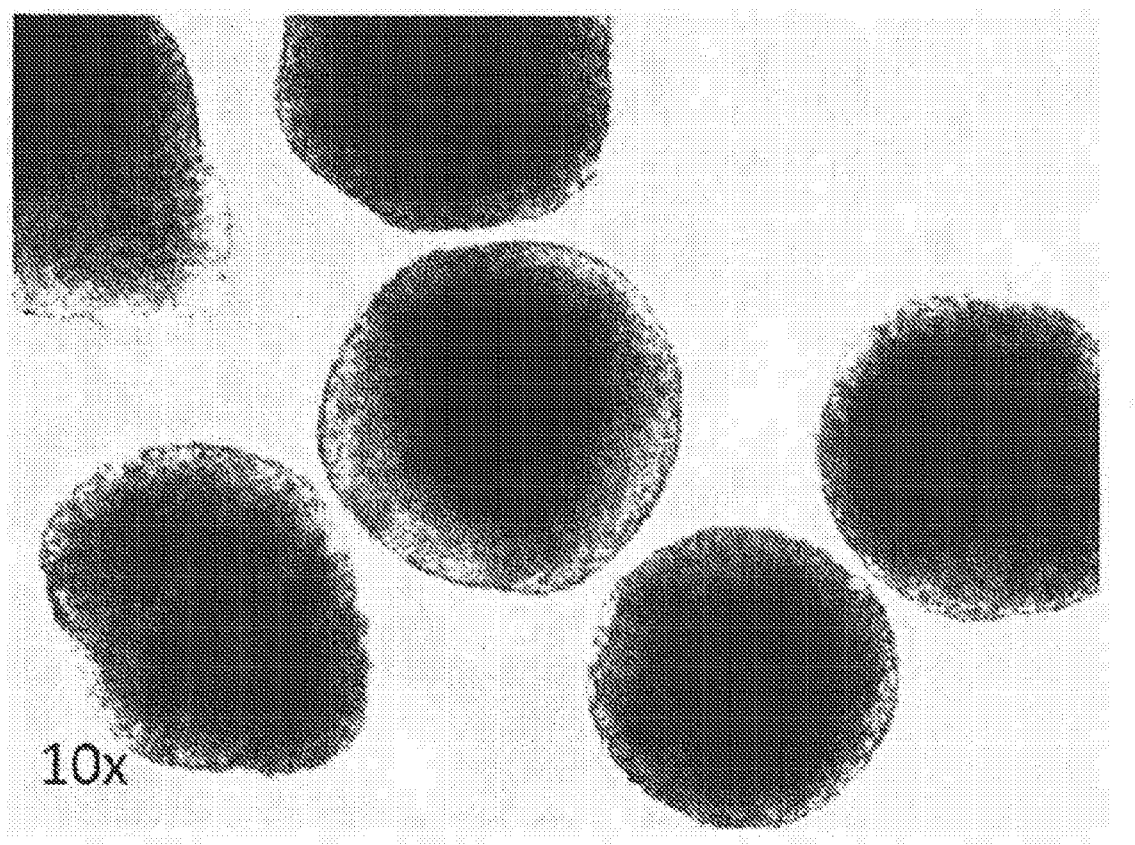
FIG. 6 shows EB formed from iPS(IMR90)-4 cells that have been cultured in 3D discontinuous entity of the invention. The cells were cultured either in floating culture to form EBs or on 2D coatings without CNF.
Figure 7:
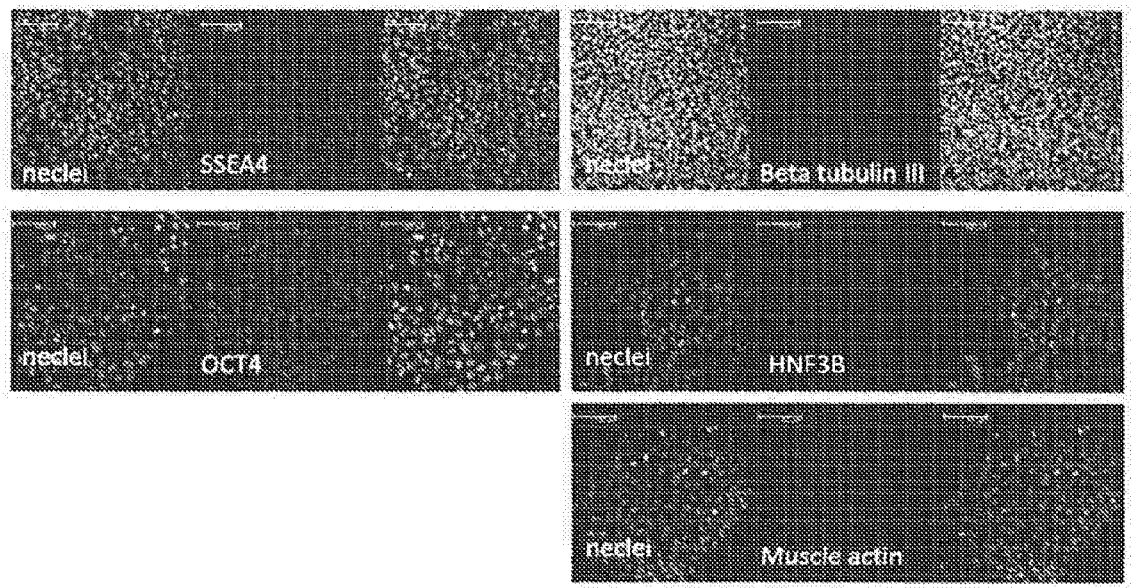
FIG. 7 shows iPS(IMR90)-4 cells transferred from 3D culture in 3D discontinuous entity of the invention to 2D laminin 511 express SSEA4 and OCT4 but not beta-tubulin III, muscle actin and HNF3B. Scale bar: 100 μm.
Figure 8:
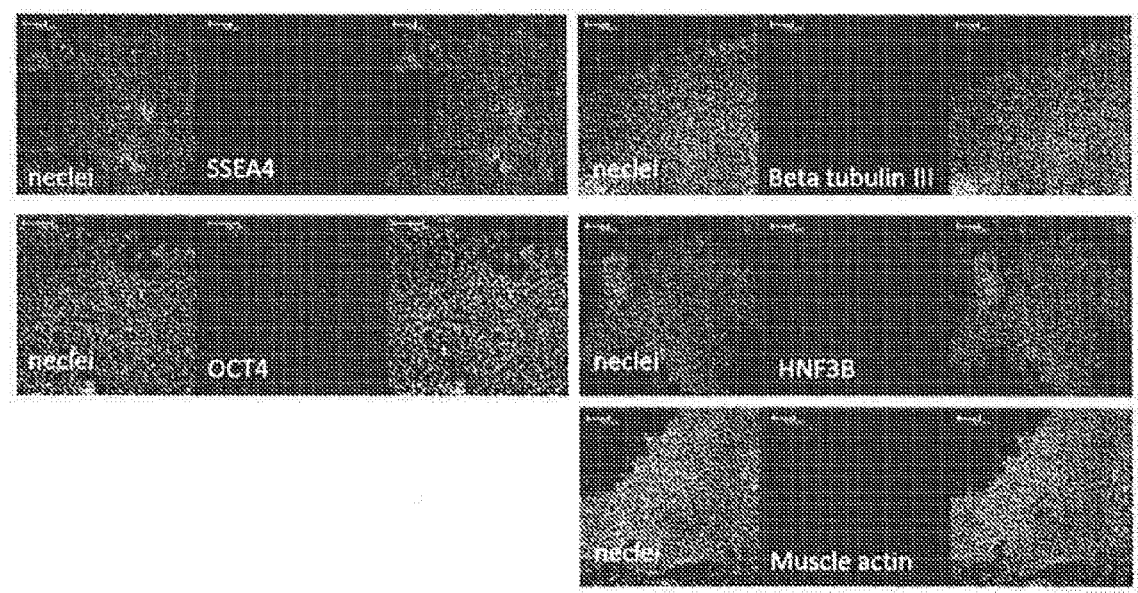
FIG. 8 shows iPS(IMR90)-4 cells transferred from 3D culture in 3D discontinuous entity of the invention to 2D laminin 521 express SSEA4 and OCT4 but not beta-tubulin III, muscle actin and HNF3B. Scale bar: 100 μm.
Figure 9:
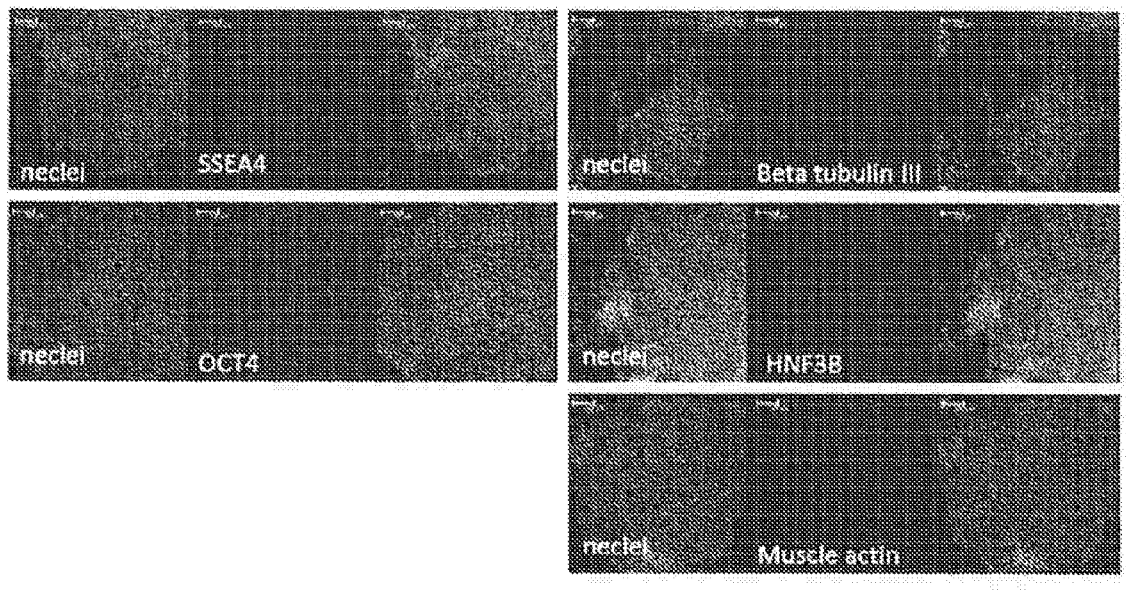
FIG. 9 shows iPS(IMR90)-4 cells transferred from 3D culture in 3D discontinuous entity of the invention to 2D Matrigel express SSEA4 and OCT4 but not beta-tubulin III, muscle actin and HNF3B. Scale bar: 100 μm.
Figure 10:
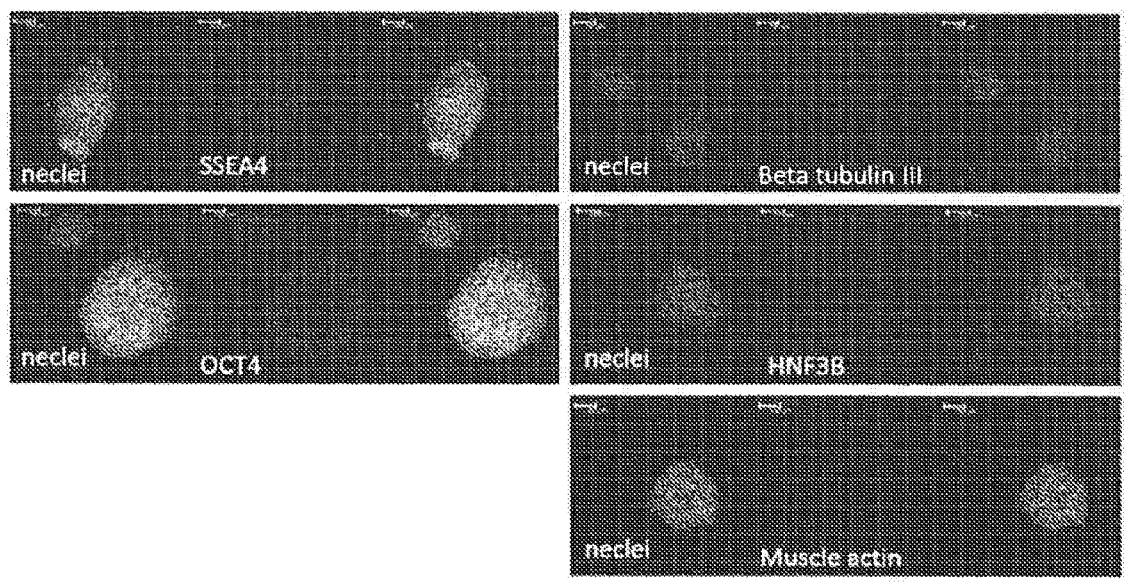
FIG. 10 shows iPS(IMR90)-4 cells transferred from 3D culture in 3D discontinuous entity of the invention to 2D vitronectin express SSEA4 and OCT4 but not beta-tubulin III, muscle actin and HNF3B. Scale bar: 100 μm.
Figure 11:
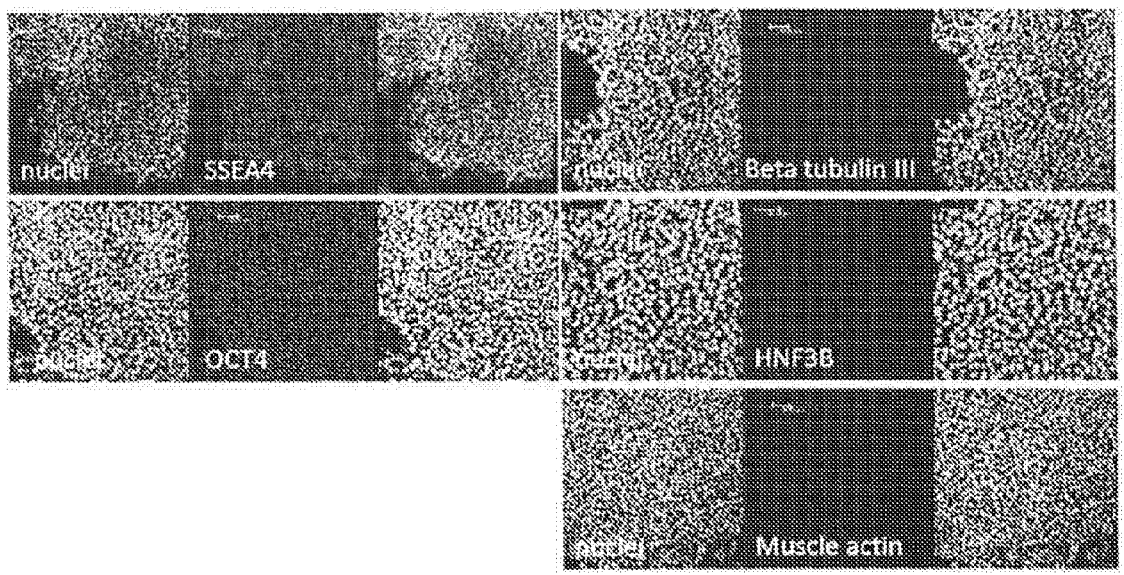
FIG. 11 shows WA07 cells transferred from 3D culture in 3D discontinuous entity of the invention to 2D laminin 511 express SSEA4 and OCT4 but not beta-tubulin III, muscle actin and HNF3B. Scale bar: 50 μm.
Figure 12:
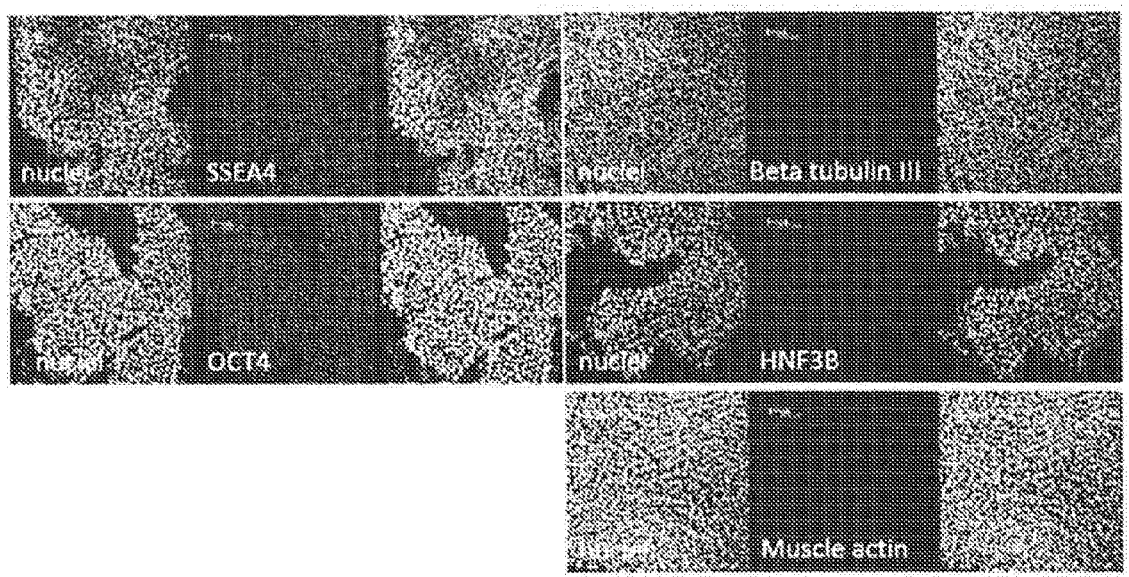
FIG. 12 shows WA07 cells transferred from 3D culture in 3D discontinuous entity of the invention to 2D laminin 521 express SSEA4 and OCT4 but not beta-tubulin III, muscle actin and HNF3B. Scale bar: 50 μm.
Figure 13:
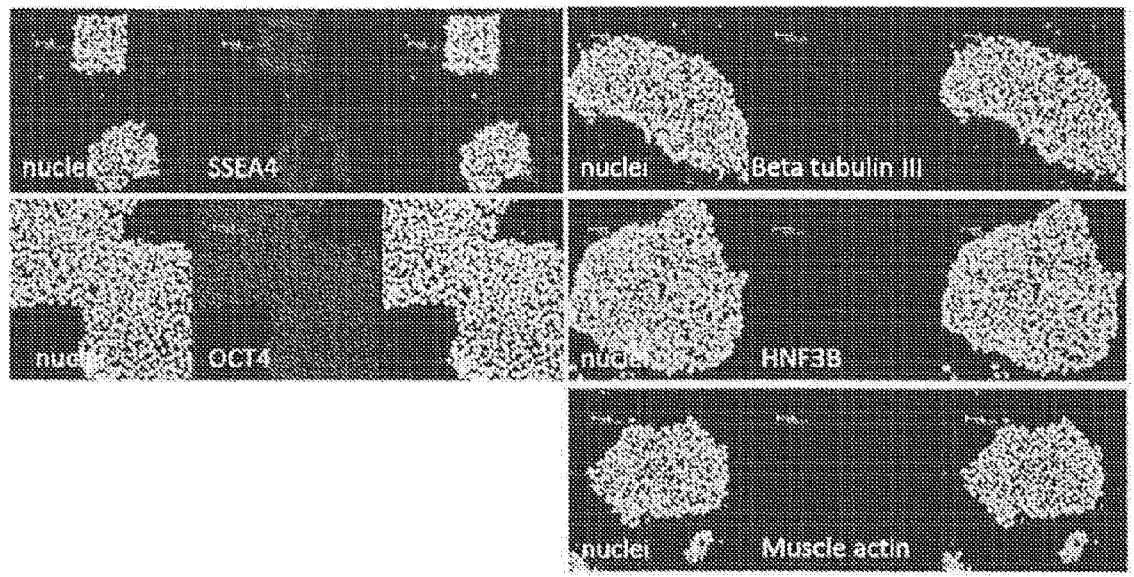
FIG. 13 shows WA07 cells transferred from 3D culture in 3D discontinuous entity of the invention to 2D Matrigel express SSEA4 and OCT4 but not beta-tubulin III, muscle actin and HNF3B. Scale bar: 50 μm.
Figure 15:
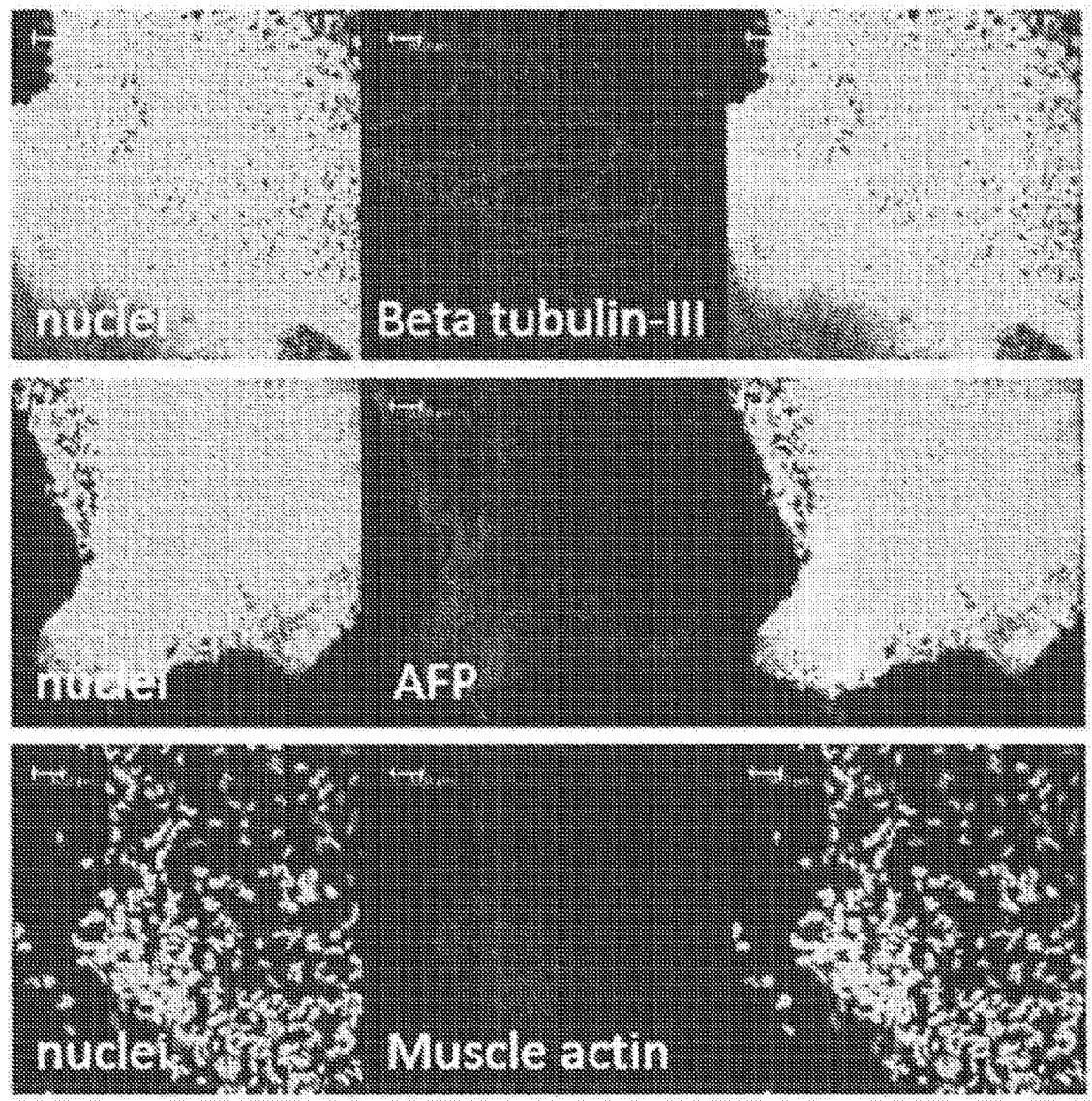
FIG. 15 shows In vitro differentiation of iPS(IMR90)-4 cells via EB formation: iPS(IMR90)-4 cells were first cultured in 3D discontinuous entity of the invention and the culturing was continued on Matrigel-coated dishes. The embryoid bodies were formed in floating culture. The differentiated cells express beta-tubulin III, muscle actin and HNF3B. Scale bar: 50 μm.

To form embryoid bodies, two methods were used. In the direct method, the cell spheroids recovered from CNF hydrogel were directly cultured for 4 weeks in IMDM medium containing 15% HyClone Defined FBS. In the indirect method, cells were first recovered from the CNF hydrogel and then cultured in Matrigel-coated dishes. The 2D cell colonies were then used to form embryoid bodies in IMDM medium on Matrigel coated dishes containing 15% HyClone Defined FBS for 4 weeks (FIGS. 6 and 15).

Example 8

Teratoma Formation

The cell spheroids from 3D culture were harvested after cellulose treatment, collected into tubes and pelleted by centrifugation. Teratoma tests were performed at the Biomedicum stem cell centre, Finland.

REFERENCES

1. Thomson, J. A. et al. Embryonic stem cell lines derived from human blastocysts. Science 282, 1145-1147 (1998).
2. Takahashi, K. et al. Induction of pluripotent stem cells from adult human fibroblasts by defined factors. Cell 131, 861-872 (2007).
3. Yu, J. et al. Induced pluripotent stem cell lines derived from human somatic cells. Science 318, 1917-1920 (2007).
4. Xu, C. et al. Feeder-free growth of undifferentiated human embryonic stem cells. Nature biotechnology 19, 971-974 (2001).
5. Ludwig, T. E. et al. Derivation of human embryonic stem cells in defined conditions. Nature biotechnology 24, 185-187 (2006).
6. Braam, S. R. et al. Recombinant vitronectin is a functionally defined substrate that supports human embryonic stem cell self-renewal via alphavbeta5 integrin. Stem Cells 26, 2257-2265 (2008).
7. Rodin, S. et al. Long-term self-renewal of human pluripotent stem cells on human recombinant laminin-511. Nature biotechnology 28, 611-615 (2010).
8. Melkoumian, Z. et al. Synthetic peptide-acrylate surfaces for long-term self-renewal and cardiomyocyte differentiation of human embryonic stem cells. Nature biotechnology 28, 606-610 (2010).
9. Villa-Diaz, L. G. et al. Synthetic polymer coatings for long-term growth of human embryonic stem cells. Nature biotechnology 28, 581-583 (2010).
10. Walther, A., Timonen, J. V., Diez, I., Laukkanen, A. & Ikkala, O. Multifunctional high-performance biofibers based on wet-extrusion of renewable native cellulose nanofibrils. Adv Mater 23, 2924-2928 (2011).
11. Pahimanolis, N. et al. Surface functionalization of nanofibrillated cellulose using click-chemistry approach in aqueous media. Cellulose 18, 1201-1212 (2011).
12. Filpponen, I. et al. Generic method for modular surface modification of cellulosic materials in aqueous medium by sequential "click" reaction and adsorption. Biomacromolecules 13, 736-742 (2012).
13. Yu, J. et al. Human induced pluripotent stem cells free of vector and transgene sequences. Science 324, 797-801 (2009).

---

The invention claimed is:

1. A three-dimensional discontinuous entity for culturing of cells comprising
   a. an aqueous medium comprising a mixture of a first and second aqueous medium; and
   b. hydrogel bodies comprising cellulose nanofibrils and/or derivatives thereof suspended in the aqueous medium, the cellulose nanofibrils being obtained from plant-derived, mechanically disintegrated cellulose, wherein the cellulose nanofibrils and/or derivatives thereof are suspended in the aqueous medium, wherein the hydrogel bodies have discontinuous structures, are separate or interconnected, and have different sizes and forms.

2. The three-dimensional discontinuous entity according to claim 1, wherein the ratio of total volume of the hydrogel bodies to total volume of the three-dimensional discontinuous entity is 10%-99% (v/v).

3. The three-dimensional discontinuous entity according to claim 1, wherein the hydrogel bodies are interconnected.

4. The three-dimensional discontinuous entity according to claim 1, wherein a yield stress of the three-dimensional discontinuous entity is lower than a yield stress of the corresponding continuous hydrogel in the same conditions.

5. The three-dimensional discontinuous entity according to claim 1, wherein a yield stress of the three-dimensional discontinuous entity is 1-95% of a yield stress of the corresponding continuous hydrogel in the same conditions.

6. The three-dimensional discontinuous entity according to claim 1, wherein the diameter of the cellulose nanofibrils is less than 1 μm.

7. The three-dimensional discontinuous entity according to claim 1, wherein the cellulose nanofibrils comprise native ion-exchanged, chemically modified or physically modified derivatives of cellulose nanofibrils or nanofibril bundles.

8. The three-dimensional discontinuous entity according to claim 1, wherein the aqueous medium is a cell culture medium comprising at least one nutrient source and at least one component required for sustaining undifferentiated, differentiating or differentiated cell growth.

9. A cell culture matrix comprising a cell or cells and/or a tissue or tissues and a three-dimensional discontinuous entity according to claim 1, wherein the cell or cells and/or tissue or tissues are present at least partially embedded in said entity in a three-dimensional or two-dimensional arrangement.

10. The cell culture matrix according to claim 9, wherein the cells are differentiated or undifferentiated mammalian cells.

11. The cell culture matrix according to claim 9, wherein the cells are undifferentiated stem cells.

12. The cell culture matrix according to claim 9, wherein the cells are embryonic stem cells or induced pluripotent stem cells.

13. The cell culture matrix according to claim 9, wherein the cells are human cells or non-human cells.

14. The cell culture matrix according to claim 13 wherein the cells are non-human embryonic stem cells or induced pluripotent stem cells.

15. A kit comprising
   a first container comprising the three-dimensional discontinuous entity according to claim 1 or the three-dimensional discontinuous entity according to claim 1 in dehydrated form such as dry powder, concentrated granulate, or concentrated hydrogel body, and
   a second container comprising cellulase.

16. The three-dimensional discontinuous entity of claim 1 further comprising one or more components selected from the group consisting of a cell culture medium, an extra cellular matrix component, a serum, growth factor, a protein, an antibiotic, and a preservative.

17. The three-dimensional discontinuous entity of claim 1, wherein the discontinuous structure of the hydrogel bodies is a homogeneous structure broken by mixing.

18. The three-dimensional discontinuous entity of claim 1, wherein the hydrogel bodies are interconnected hydrogel bodies having aqueous cavities positioned therebetween.

19. The three-dimensional discontinuous entity of claim 1, wherein the hydrogel bodies are loosely connected and floating within the mixture.

20. The three-dimensional discontinuous entity of claim 1, further comprising cells, the hydrogel bodies being indirectly connected to one another via the cells.

21. The three-dimensional discontinuous entity of claim 1, wherein the second aqueous medium is a cell culture medium.

22. The three-dimensional discontinuous entity of claim 1, wherein proteases are undetectable in the three-dimensional discontinuous entity.

23. The three-dimensional discontinuous entity of claim 1, wherein the cellulose nanofibrils are sterilized.

* * * * *

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
aatctccagg ggcaccatt                                                   19

<210> SEQ ID NO 2
<211> LENGTH: 18
<212> TYPE: DNA
<213> ORGANISM: Artificial Sequence
<220> FEATURE:
<223> OTHER INFORMATION: primer

<400> SEQUENCE: 2
cgctggctcc cactttgt                                                    18

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gcagaaggcc tcagcaccta                                                  20

<210> SEQ ID NO 4
<211> LENGTH: 19
<212> TYPE: DNA
<213> ORGANISM: Artificial Sequence
<220> FEATURE:
<223> OTHER INFORMATION: primer

<400> SEQUENCE: 4
ggttcccagt cgggttcac                                                   19
```

```
<210> SEQ ID NO 5
<211> LENGTH: 19
<212> TYPE: DNA
<213> ORGANISM: Artificial Sequence
<220> FEATURE:
<223> OTHER INFORMATION: primer

<400> SEQUENCE: 5
cagtgcccga aacccacac                                                    19

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
ggagacccag cagcctcaaa                                                   20
```